(12) United States Patent
Blanchard-Desce et al.

(10) Patent No.: US 8,535,643 B2
(45) Date of Patent: Sep. 17, 2013

(54) FLOURESCENT DENDRIMER COMPOUNDS AND USE OF SUCH COMPOUNDS IN MULTI-PHOTON DEVICES OR PROCESSES

(75) Inventors: Mireille Blanchard-Desce, Rennes (FR); Martinus Werts, Rennes (FR); Olivier Mongin, Rennes (FR); Jean-Pierre Majoral, Ramonville Saint-Agne (FR); Anne-Marie Caminade, Toulouse (FR); Rama Krishna Thatavarthy, Toulouse (FR)

(73) Assignees: Universite de Rennes 1, Rennes Cedex (FR); CNRS, Rennes Cedex (FR)

( * ) Notice: Subject to any disclaimer, the term of this patent is extended or adjusted under 35 U.S.C. 154(b) by 678 days.

(21) Appl. No.: 12/160,612

(22) PCT Filed: Jan. 10, 2007

(86) PCT No.: PCT/EP2007/050225
§ 371 (c)(1),
(2), (4) Date: Jun. 10, 2010

(87) PCT Pub. No.: WO2007/080176
PCT Pub. Date: Jul. 19, 2007

(65) Prior Publication Data
US 2010/0266506 A1  Oct. 21, 2010

(30) Foreign Application Priority Data

Jan. 13, 2006  (FR) ..................................... 06 00339

(51) Int. Cl.
*A61B 5/00* (2006.01)
*H01J 3/14* (2006.01)
*C08G 75/00* (2006.01)

(52) U.S. Cl.
USPC ............................. 424/9.6; 250/216; 528/373

(58) Field of Classification Search
None
See application file for complete search history.

(56) References Cited

U.S. PATENT DOCUMENTS 6,969,528 B1 * 11/2005 Majoral et al. ................ 424/486
2005/0214767 A1   9/2005 Trevisiol et al.

OTHER PUBLICATIONS

Krishna, Thatavarathy R. et al, Water-Soluble Dendrimeric Two-Photon Tracers for In Vivo Imaging, Angew.Chem. Int. Ed., 2006, vol. 45, pp. 4645-4648 (published online: Jun. 21, 2006 annotated on p. 4647).*

Loup, Christophe et al, Preparation of Water-Soluble cationic Phosphorus-Containing Dendrimers as DNA Transfecting Agents, Chem. Eur. J., 1999, vol. 5, pp. 3644-3650.*
Turrin et al, Surface, core, and structure modifications of phosphorus-containing dendrimers. Influence on the thermal stability., Tetrahedron, 2003, vol. 59, pp. 3965-3973.*
Launay et al, synthesis of bowl-shaped dendrimers from generation 1 to generation 8, Journal of Organometallic Chemistry, 1997, vol. 529, pp. 51-58.*
Mongin, Olivier et al, A modular approach to two-photon absorbing organic nanodots: brilliant dendrimers as an alternative to semiconductor quantum dots?, Chem. Commun., 2006, pp. 915-917.*
Mongin O, Porres L, Moreaux L, Mertz J, Blanchard-Desce M, "Synthesis and Photophysical Properties of New Conjugated Fluorophores Designed for Two-Photon-Excited Fluorescence" Organic Letters, vol. 4, No. 5, 2002, pp. 719-722.
Werts M H, Gmough, S, Mongin O, Pons T, Blanchard-Desce, M., "Strong Modulation of Two-Photon Excited Fluorescence of Quadripolar Dyes by (De)Protonation" Journal of the American Chemical Society, vol. 126, 2004, pp. 16294-16295.
Maraval V, Laurent R, Marchand P, Caminade A-M, Majoral J-P, "Accelerated Methods of Synthesis of Phosphorous-Containing Dendrimers," Journal of Organometallic Chemistry, vol. 690, No. 10, 2005, pp. 2458-2471.
Katan C., Terenziani F., Mongin O., Werts M.G.V, Porres L., Pons, T., Mertz, J., Tretiak S., Blanchard-Desce, M. "Effects of (Multi)Branching of Dipolar Chromophores on Photophysical Properties and Two-Photon Absorption," J. Phys. Chem. A., vol. 109, 2005, pp. 3024-3037.
Le Droumaguet C, Mongin O, Werts MHV., Blanchard-Desce, M. "Towards Smart Multiphoton Fluorophores: Strongly Solvatochromic Probes for Two-Photon Sensing of Micropolarity," Chem. Commun. 2005, pp. 2802-2804.
Brousmiche, DW, Serin, JM, Frechet JMJ, He, GS, Lin TC, Chung SJ, Prasad, PN, Kannan, R, Tan LS, Fluorescence Resonance Energy Transfer in Novel Multiphoton Absorbing Dendritic Structures,: J. Phys. Chem. B., vol. 108, 2004, pp. 8592-8600.
Caminade AM, Majoral JP, "Water-Soluble Phosphorous-containing Dendrimers" Progress in Polymer Science, Vo. 30, 2005, pp. 491-505.
English translation of the International Preliminary Report on Patentability, (Feb. 26, 2007).

* cited by examiner

Primary Examiner — Michael G Hartley
Assistant Examiner — Sun Y Kim
(74) Attorney, Agent, or Firm — Thomas Horstemeyer, LLP

(57) ABSTRACT

Fluorescent chemical compound composed of an n-generation dendrimer, n being a non-zero integer, exhibiting: —at least one central nucleus (N) with a valency of m, selected from the group consisting of—at least one first, non-chromophoric unit (X) with a valency of m', and—at least one second unit (Y) which exhibits two-photon absorption properties, with a valency of m".

12 Claims, 15 Drawing Sheets

*Reagents and conditions*: (a) 2-methyl-3-butyn-2-ol, Pd(PPh$_3$)$_2$Cl$_2$, CuI, toluene/Et$_3$N, 40°C, 16 h (87%); (b) NaOH, toluene/i-PrOH, reflux, 0,5 h (44%); (c) Pd(PPh$_3$)$_2$Cl$_2$, CuI, toluene/Et$_3$N 40°C, 3,5h (37%); (d) KOH, toluene/i-PrOH, reflux, 1h (87%); (e) hydroquinone (3 equiv.), DEAD, PPh$_3$, THF, 20°C, 16h (51%); (f) Pd(PPh$_3$)$_2$Cl$_2$, CuI, toluene/Et$_3$N 40°C, 16h (57%)

G1

G2

G3

G4

*Reagents and conditions*: (a) Pd(PPh$_3$)$_2$Cl$_2$, CuI, toluene/Et$_3$N,; (b) KOH, toluene/*i*-PrOH,reflux; (c) 4-hydroxbenzadehyde, DEAD, PPh$_3$, THF, 20°C; (d) I$_2$, CH$_2$Cl$_2$, NaHCO$_3$, 20°C;(e) Pd(PPh$_3$)$_2$Cl$_2$, CuI, toluene/Et$_3$N.

FLOURESCENT DENDRIMER COMPOUNDS AND USE OF SUCH COMPOUNDS IN MULTI-PHOTON DEVICES OR PROCESSES

CROSS REFERENCE TO RELATED APPLICATION

This application claims priority to "Fluorescent Dendrimer Compounds and Use of Such Compounds in Multiphoton Devices or Processes," having serial number PCT/EP2007/050225, filed on Jan. 10, 2007. This application also claims priority to and benefit of French Application entitled "Fluorescent Dendrimer Compounds and Use of Such Compounds in Multiphoton Devices or Processes", having Application No. 06/00339, filed on Jan. 13, 2006, which is incorporated by reference in its entirety.

The invention relates to the field of the development and production of fluorescent compounds ("fluorophores") having properties making them capable of being implemented in multiphoton processes and devices and in particular biophotonic processes and devices.

The study of the major cell functions such as, for example, genome expression, membrane trafficking and the study of the mobility of cells and their organization into tissues make it necessary to localize, measure and quantify, in vivo, at the microscopic and nanoscopic scale, the dynamics and interactions between molecules of biological interest (proteins, nucleic acids, lipids, ions, etc.).

Although classic fluorescence microscopy, which implements markers (fluorophores) excitable by single-photon excitation, is a powerful tool for imaging of living matter, it nevertheless has a number of drawbacks, limiting its benefit in this field of application.

First, it often implements probes excitable in the ultraviolet range or in the blue portion of the visible spectrum. Such an excitation in this field can be toxic for living tissue.

Second, it allows only an observation of limited depth in the living tissue due to the greater diffusion of visible light than infrared light, and the intrinsic absorption of biomolecules.

Third, it can induce endogenous fluorescence of living tissue, which interferes with observation.

Multiphoton microscopy makes it possible to overcome these problems by the two-photon excitation fluorescence technique (hereinafter sometimes referred to as "TPEF").

This technique is based on the concept that certain atoms or molecules can simultaneously absorb two photons. This two-photon absorption property (hereinafter sometimes referred to as "TPA") of certain molecules is characterized by their effective TPA cross-section, denoted $\sigma_2$.

Thus, certain fluorescent molecules (fluorophores) excitable by a photon of energy $h\nu$ and of wavelength $\lambda$ are also capable of being excited simultaneously by two photons of energy $h\nu/2$ and of wavelength $2\lambda$. A single-photon excitation in the UV range-blue portion of the visible spectrum can thus be replaced by biphotonic excitation in the red-near infrared range, which is non-toxic for living tissue and generates less endogenous fluorescence of the samples observed.

In addition, the non-linear character of the absorption localizes the excitation, and therefore the emission of fluorophores, at the focal point of the laser in the sample to be studied. Thus, three-dimensional images of biological tissue in vivo can be obtained with a resolution on the order of the micrometer to depths of at least 500 µm, without causing damage to said tissue.

This non-linear character of the absorption also allows for fine three-dimensional spatial resolution.

In practice, the two-photon absorption observed in certain atoms or particles has make it possible to develop numerous technologies in a wide variety of fields, such as 3-dimensional microfabrication, optical data storage, photodynamic therapy and optical limitation (i.e. protection from laser aggression).

The development of TPEF has therefore paved the way for the development of effective processes and devices adapted to the living medium (and therefore called "biophotonic" processes and devices) in the field of cell imaging (microscopy, 3D imaging), in the field of diagnostic tools (fluorescent probes, absorbent particles, biochips), and in the field of therapy (phototherapy or photodynamic therapy).

However, it is noted that there is a lack on the market of fluorophore compounds specifically suitable for these new technologies.

Indeed, the fluorophore compounds currently used in the multiphoton techniques are optimized for the classic fluorescence techniques, i.e. implementing single-photon excitation.

These classic compounds of the prior art are not optimized for the multiphoton techniques and in particular not for biphotonic techniques.

In practice, these compounds have mediocre TPA properties in the spectral window of biological interest (700 to 1200 nm) and must be used at concentrations capable of disturbing the medium observed. Their use in biphotonic excitation therefore requires, owing to their weak response to this type of excitation, high light intensities and/or high chromophore concentrations of in order to generate a detectable signal.

The prior art also describes luminescent nanoparticles with a radius of up to 3 nanometers and formed by semi-conductive nanocrystals, known to a person skilled in the art as "quantum dots". These quantum dots, which are in particular described in the article of Daniel R. Larson et al., "Water-Soluble Quantum dots for multiphoton fluorescence imaging in vivo"; Science 2003 Volume 300, 1434-1436, have seen spectacular developments. Indeed, it was shown that such systems could have very high effective TPEF cross-sections ($\sigma_2\phi$) and in practice currently reaching 47000 GM, thus enabling them to be used in biphotonic imaging of living tissue.

However, these quantum dots also have a number of disadvantages.

First, because they include heavy metals such as cadmium in their structure, they have a non-negligible toxicity with regard to living tissue. Their synthesis processes correspondingly have the disadvantage of implementing toxic products as well.

Second, these quantum dots also have the disadvantage of forming structures that are not easily functionalisable. In particular, these structures do not easily lend themselves to covalent bonding on small molecules for targeting, at the molecular scale, and without disturbing them, biological targets identified, such as proteinacious complexes or DNA, for example. This aspect considerably limits the use of these quantum dots in biological applications.

Finally, in order to be protected from the ambient environment, they also have the disadvantage of having to be encapsulated in polymers, which complicates their production.

The main objective of this invention is to propose new fluorescent chemical compounds specifically adapted for implementation in multiphoton and in particular biphotonic techniques.

In particular, an objective of this invention is to describe such compounds that make it possible to ensure the safety of the techniques in the context in which they are used, while having a high sensitivity and selectivity.

In particular, an objective of this invention is to propose such compounds that simultaneously have high fluorescence quantum efficiencies (φ) in a wide variety of media (including water in the case of water-soluble derivatives), effective TPA cross-sections ($\sigma_2$) optimized for the spectral range of biological interest (700-1200 nm), consequently high brightness ($\sigma_2 \cdot \phi$), good photostability and low toxicity.

High brightness indeed makes it possible to reduce the concentration of fluorescent molecular markers and/or the excitation intensity, which is highly desirable for biological imaging.

Another objective of this invention is to propose an array of such fluorescent compounds capable of being applied to very different targets.

Yet another objective of this invention is to propose such compounds capable of producing light signals that can be distinguished by their emission wavelengths and thus allowing the implementation of multiplexing (the light flow emanating from the sample marked by a plurality of fluorophores can thus simultaneously transport a plurality of signals separable by filters).

Yet another objective of this invention is to propose organic compounds capable of being used in any process or device implementing two-photon or even three-photon absorption, with an effective TPA cross-section ($\sigma_2$) and a brightness (product of the effective TPA cross-section, $\sigma_2$, by the fluorescence quantum efficiency, φ) comparable to those of inorganic quantum dots.

Another objective of this invention is to propose such compounds that occupy the smallest possible volume.

Yet another objective of this invention is to propose such compounds enabling grafting of a variety of functional groups having different types of functionalities.

In particular, a specific objective of this invention is to present such chemical compounds that are soluble in water owing to such functional groups.

These various objectives are achieved by the invention, which relates to any fluorescent chemical compound formed by a dendrimer of n generation(s), with n being a non-zero integer, having:

at least one central core (N) of valence m;

at least one first non-chromophoric pattern (X), of valence m', with m patterns (X) being directly bound to said central core (N) and/or x patterns forming at least one generation of said dendrimer; and at least one second pattern (Y) having two-photon absorption properties, of valence m", with m patterns (Y) being directly bound to said central core (N) and/or y patterns (Y), belonging to, or forming at least one generation of said dendrimer.

The invention therefore covers the cases in which non-chromophoric patterns (X) or chromophoric patterns (Y) are directly bound to the core (N). According to the nomenclature used for dendrimers, these patterns do not form a "generation" of the dendrimer.

X and y are of course integers, identical or different and refer to the number of respectively chromophoric and non-chromophoric patterns involved in the structure of the generations of the fluorescent dendrimer compounds according to the invention. It should be understood that these integers can vary considerably according to the valences of these patterns (X) and (Y) and that of the core (N).

This invention therefore consists in producing a fluorescent dendrimer (i.e. having, in a solvent, a fluorescence quantum efficiency, φ, greater than 10%), having at least two types of units (patterns), namely non-chromophoric patterns, i.e. not having two-photon absorption properties, and patterns having such properties.

Dendrimers, also called "cascade molecules", are highly ramified functional polymers with a defined structure having a tree structure. These macromolecules are actually polymers since they are based on the repetitivity of one or more patterns. However, dendrimers differ fundamentally from classic polymers insofar as they have specific properties due to their tree structure. The molecular weight and the shape of the dendrimers can be precisely controlled. They can be given terminal functions located at the termination of the tree structures, forming a surface, making them easily accessible.

The dendrimers are developed step-by-step, from a core, by the repetition of a reaction sequence making it possible to multiply each pattern repetitively and terminal functions. Each reaction sequence forms what is called a "new generation".

The tree structure is produced by the repetition of a reaction sequence making it possible to obtain, at the end of each reaction cycle, a new generation and an increasing number of identical branches. The generations are counted from each division of a branch into at least two branches.

After several generations, the dendrimer generally takes on a globular, highly ramified and multi-functionalized form owing to the numerous terminal functions present at the periphery.

Such dendrimers have been described in particular by Launay et al., *Angew. Chem. Int.* Ed. Engl., 1994, 33, 15/16, 1589-1592, or Launay et al., *Journal of Organometallic Chemistry*, 1997, 529, 51-58.

The compounds according to the present invention form "nano objects" with a size similar to that of quantum dots, and which have fluorescence performances, in particular TPEF performances competitive to those of the structures of the prior art.

The compounds according to this invention include a large number of two-photon absorption chromophoric patterns (Y patterns). These patterns can be provided at the level of the last generation (outer generation) of the dendrimer, but also at the level of the inner generations thereof.

These chromophoric patterns can also be of a variety of types.

This invention therefore offers the possibility of modulating the properties of these compounds, by working with:
  the number and type of chromophoric patterns integrated in their structure;
  the possibility of varying their solubility in various environments by the addition, at the level of their outer layer, of solubilization groups, and
  the possibility of adding functional groups by covalent bonds capable of conferring additional functionalities of these compounds.

It should be noted that the prior art has already proposed compounds with a dendrimer structure having two-photon absorption properties.

In the article of Drobizhev et al., "Strong cooperative Enhancement of Two-Photon Absorption in dendrimers" *J. Phys. Chem. B* 2003, 107, 7540-7543, the dendrimer is faulted by a single chromophore, composed of a plurality of conjugated subchromophoric units. Such an approach does not make it possible to envisage the modularity described above. In addition, the number of chromophores integrated in such a structure remains limited.

The article of Olivier Mongin et al., "Synthesis and Two-Photon Absorption of triphenylbenzene-cored dendritic chromophores"; *Tetrahedron Letters* 44 (2003) 2813-2816, also relates to dendrimer structures formed completely from a single chromophoric pattern, and of which the TPA cross-sections $\sigma_2$ do not go above 798 GM.

The article of Alex Adronov et al., "Novel Two-Photon Absorbing Dendritic Structures", *Chem. Mater.* 2000, 12, 28-38-28-41, suggests to produce a dendrimer with a core and two generations of a benzyl pattern with two valences not having two-photon absorption properties, and of grafting 8 chromophores forming the third and last generation of said dendrimer. According to the studies described in this article, the number of chromophoric patterns per dendrimer is limited to eight, whereas the present invention makes it possible to obtain compounds having many more chromophoric patterns. In addition, the effective TPA cross-section of the dendrimer according to Adronov et al. is only 2600 GM, whereas the invention makes it possible to obtain much higher effective cross-sections. The authors are not interested in the fluorescence quantum efficiency or the brightness of the dendrimers produced. The studies described in this article were in fact designed to study the possible cooperative effect of the chromophores with one another, with respect to the TPA cross-sections, in such a structure.

Preferably, the fluorescent dendrimer compounds according to the invention have more than 3 generations. It is thus possible to obtain molecules having a larger number of chromophoric patterns and/or to add, to their outer layer, a larger number of solubilization groups.

Preferably, the valence m of the core of the compounds according to the invention is equal to 2, 3, 4, 6, 8 or 10.

Also preferably, said core (N) and/or said pattern (X) contain(s) at least one phosphorus atom.

According to the invention, said core (N) of valence m of said dendrimer is chosen from the group consisting of:

R and R', identical or different, designating a radical chosen from the group consisting of hydrogen, $C_1$ to $C_{25}$ alkyl radicals, preferably $C_1$ to $C_{12}$ alkyl radicals.

According to a particularly beneficial alternative, said core (N) is

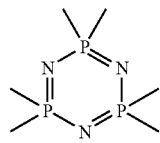

According to the invention, said non-chromophoric pattern (X) is chosen from the group consisting of:

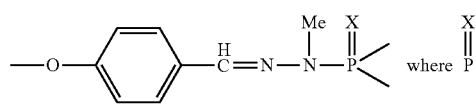

may be: 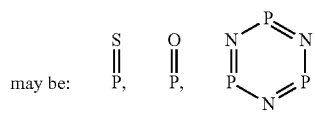

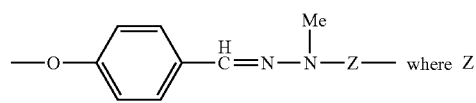

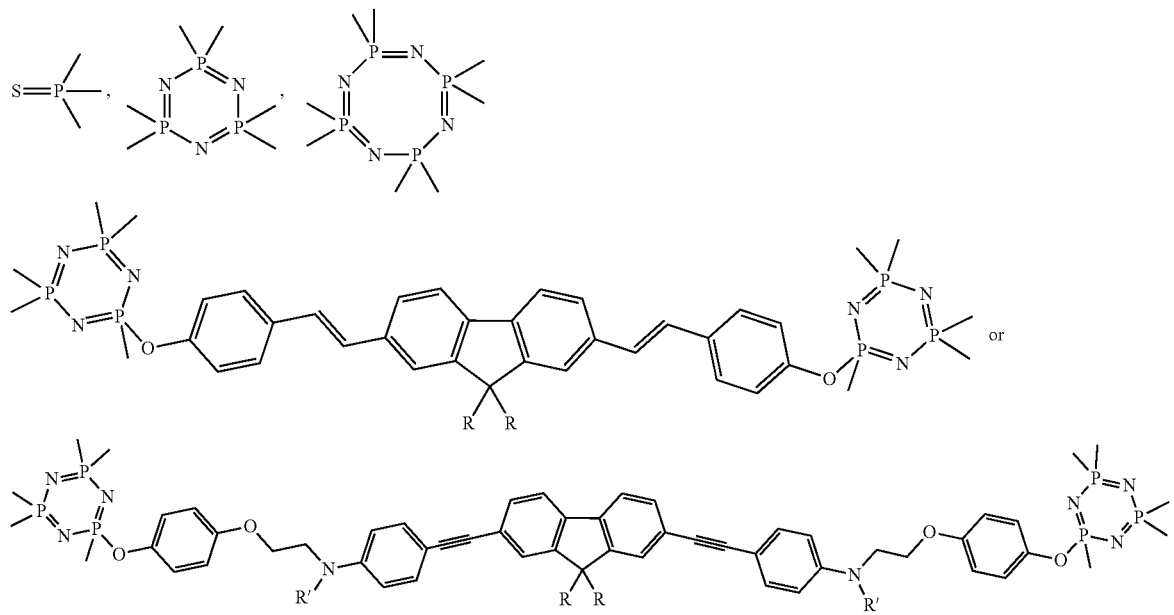

may be: 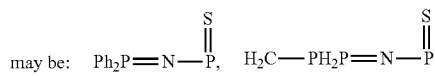

in which $F^1$ and $F^2$, identical or different, designate an electroactive grouping (electron donor or acceptor), with $F^1$ being bound to a grafting appendage and $F^2$ being bound to 0, 1 or 2 grafting appendages, and $F^1$ and $F^2$ preferably being chosen from:

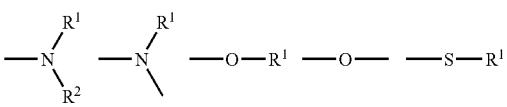

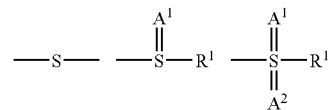

may be: 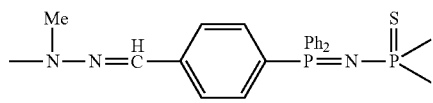

$R^1$ and $R^2$, identical or different, designating either a grafting appendage (Y2), or a radical chosen from the group consisting of hydrogen, $C_1$ to $C_{25}$ alkyl radicals, preferably $C_1$ to $C_{12}$, $(CH_2)_{m1}$—$SO_3M$, $(CH_2)_{m1}NAlk_3^+$, $(CH_2)_{m1}$—$(OCH_2$—$CH_2)_p$—OH, with M being an alkaline metal and m1 being equal to 0 or being an integer between 1 and 12, preferably between 1 and 6, and p being an integer between 1 and 25; $A^1$ and $A^2$, identical or different, representing O, NH, NAlk, $NCF_3$;

and in which,

According to the invention, said chromophoric pattern (Y) is formed by a multiphoton chromophoric radical (Y1) bound to at least one grafting appendage (Y2).

Said chromophoric radical (Y1) has one of the following two structures:

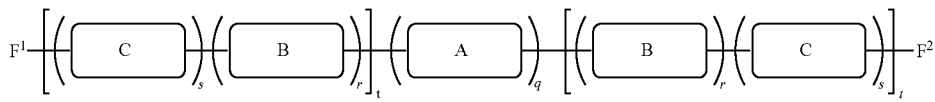

or

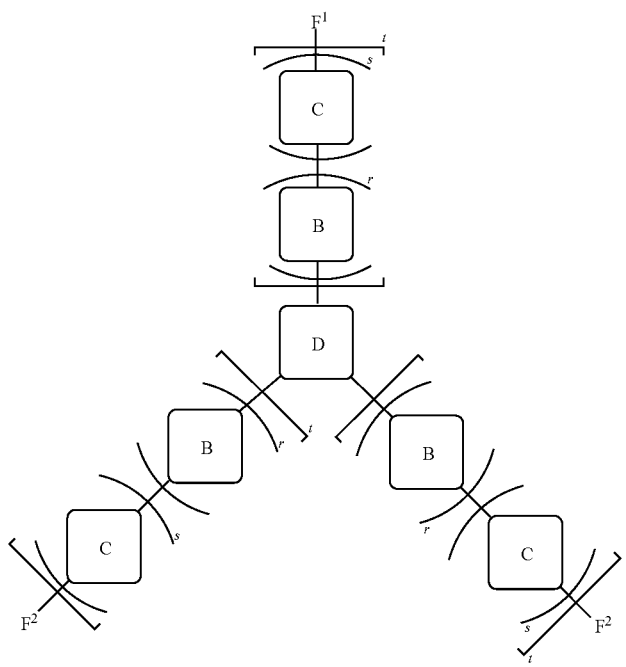

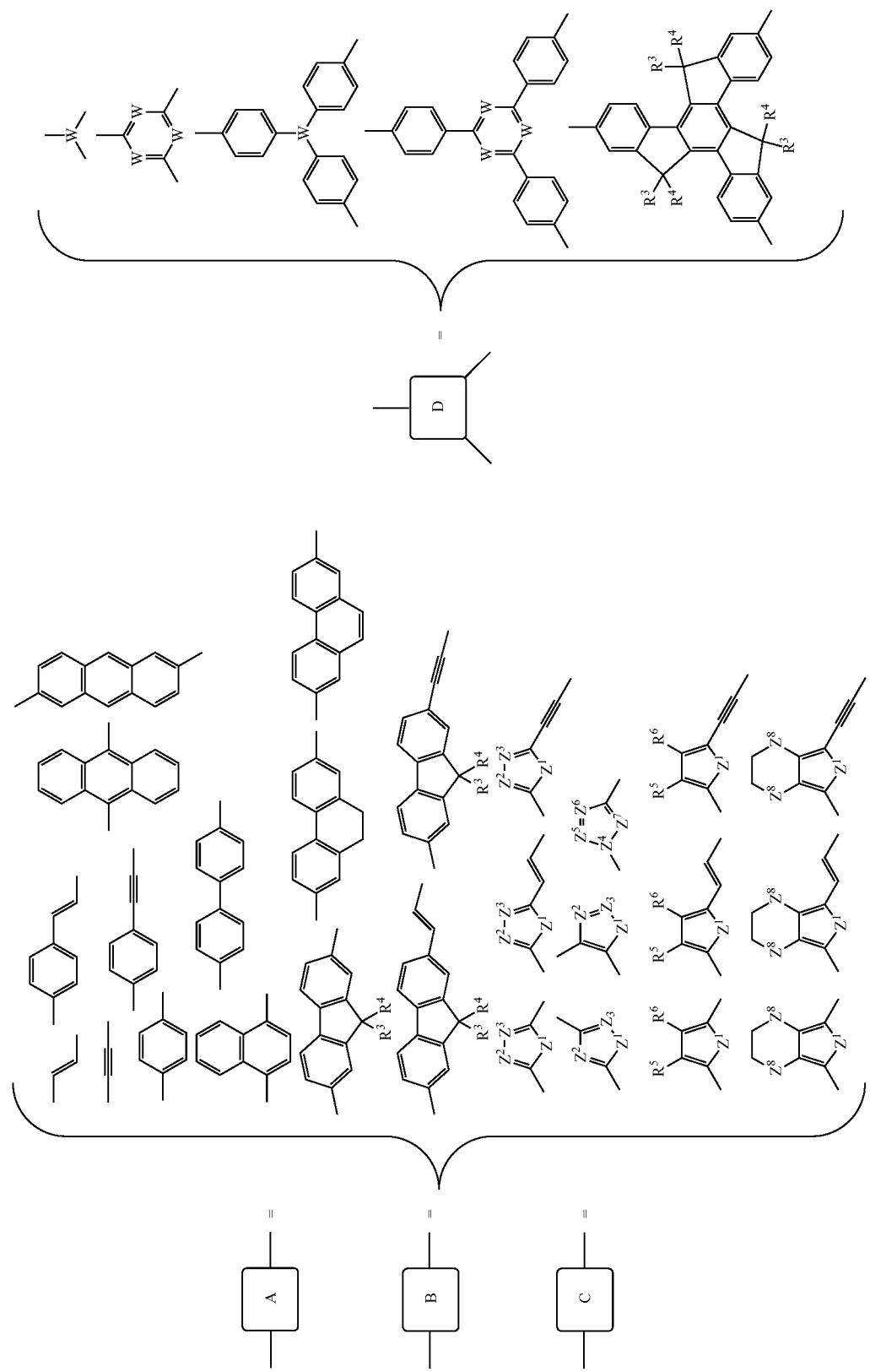

$R^3$ and $R^4$, identical or different, designating a radical chosen from the group consisting of hydrogen, $C_1$ to $C_{25}$ alkyl radicals, preferably $C_1$ to $C_{12}$, $(CH_2)_{m1}$—$SO_3M$, $(CH_2)_{m1}NAlk_3^+$, $(CH_2)_{m1}$—$(OCH_2$—$CH_2)_p$—OH, with M being an alkaline metal and m1 being equal to 0 or being an integer between 1 and 12, preferably between 1 and 6, and p being an integer between 1 and 25;

$R^5$ and $R^6$, identical or different, each representing an OH, OAlk, OAr, SH, SAlk, or SAr radical;

$Z^1$, representing O, S, NH, NAlk, NAr, PH, PAlk or PAr;

$Z^2$, $Z^3$ each representing CH, CAlk or N;

$Z^4$ representing N or P;

$Z^5$, $Z^6$, $Z^7$ each representing CH, CAlk or N;

$Z^8$ representing O or S;

q being an integer between 1 and 7;
r being an integer between 1 and 7;
s being an integer between 0 and 7;
t being an integer between 1 and 7;
W being CH or B or N or P or PO.

According to the invention, said grafting appendage (Y2) is chosen from:

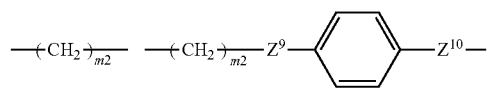

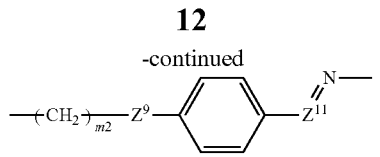

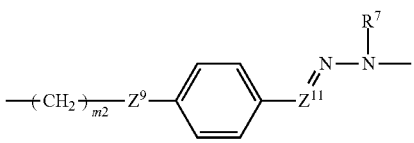

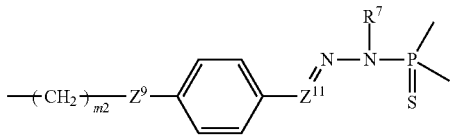

with m2 being an integer between 0 and 12, preferably between 0 and 6;

$Z^9$ and $Z^{10}$, identical or different, representing O, S, NH, NAlk, and NAr; and $Z^{11}$, representing CH, CAlk, CAr, $PAlk_2$, and $PAr_2$.

Preferably, said pattern (Y) is chosen from the group consisting of:

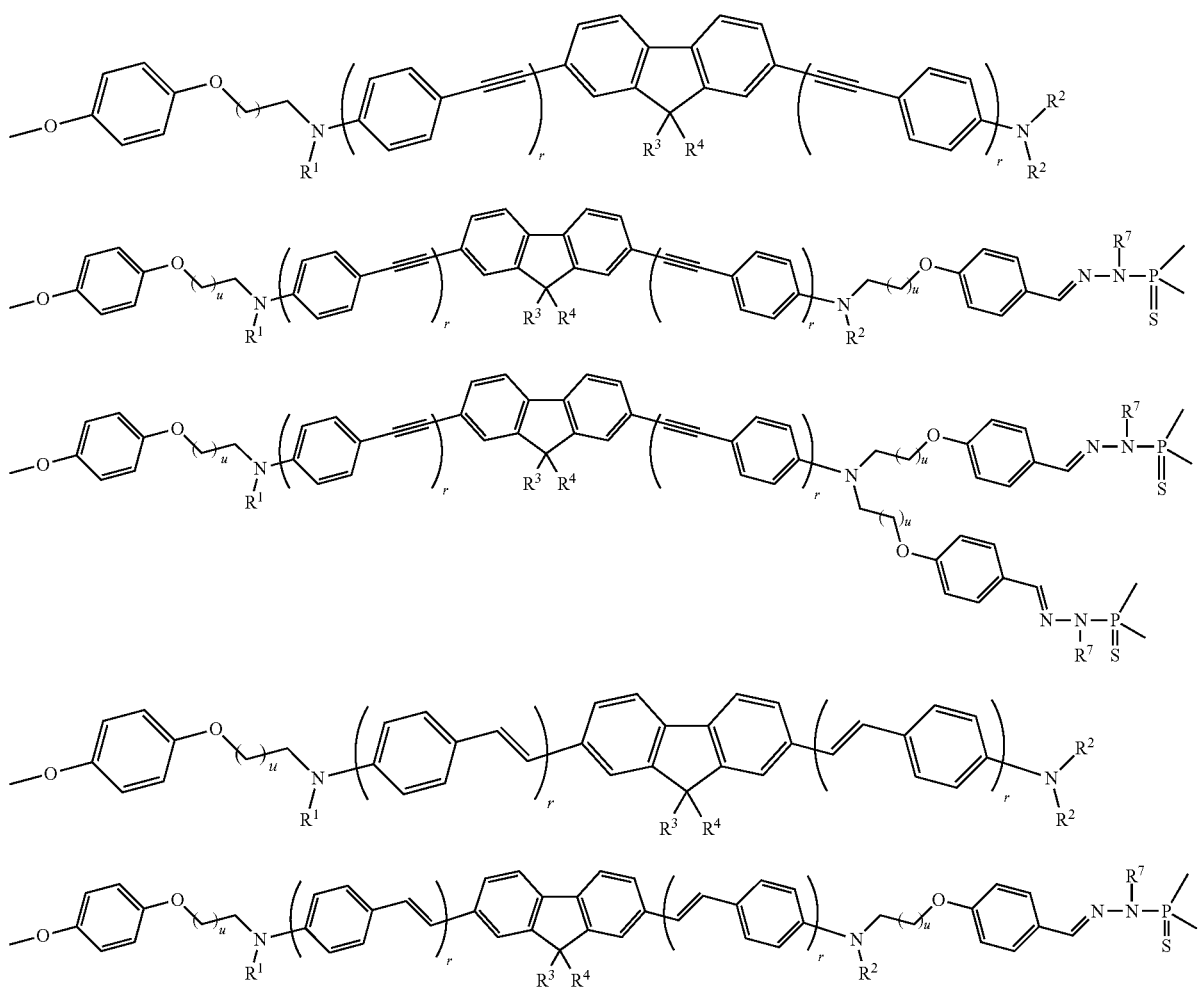

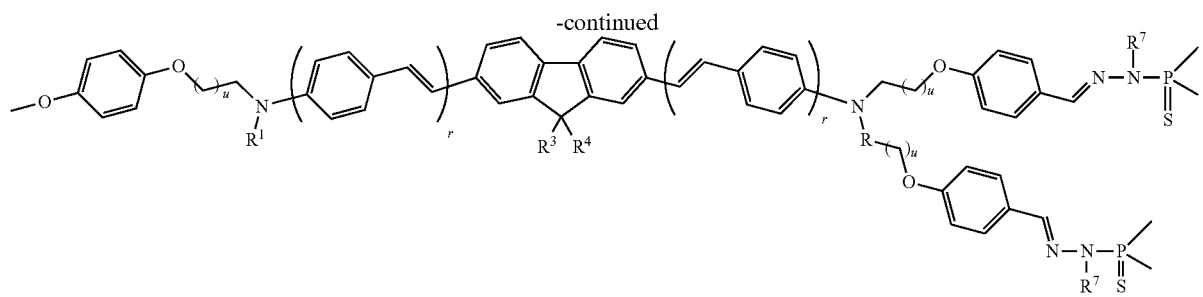

in which $R^1$, $R^2$, $R^3$, $R^4$, $R^7$ and r have the same meaning as above; and
u is an integer between 1 and 11 preferably between 1 and 5.

According to an alternative of the invention, said dendrimer has at least one third pattern (Z) forming the external layer of the generation Gn of said dendrimer and presenting either water or organic solvent solubilization properties of the dendrimer.

Preferably, said pattern (Z) is an ammonia or pyridinium or carboxylate or sulfonate pattern or a polyethyleneglycol chain.

Advantageously, the compound according to the invention satisfies any one of the following formulas:

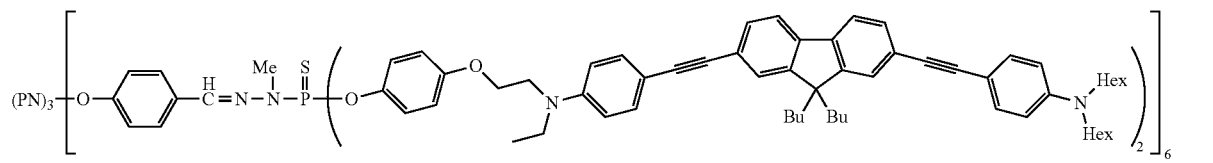

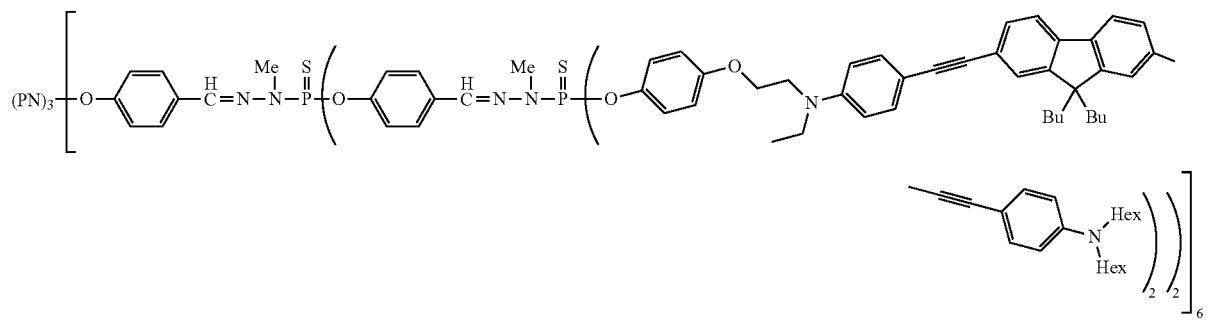

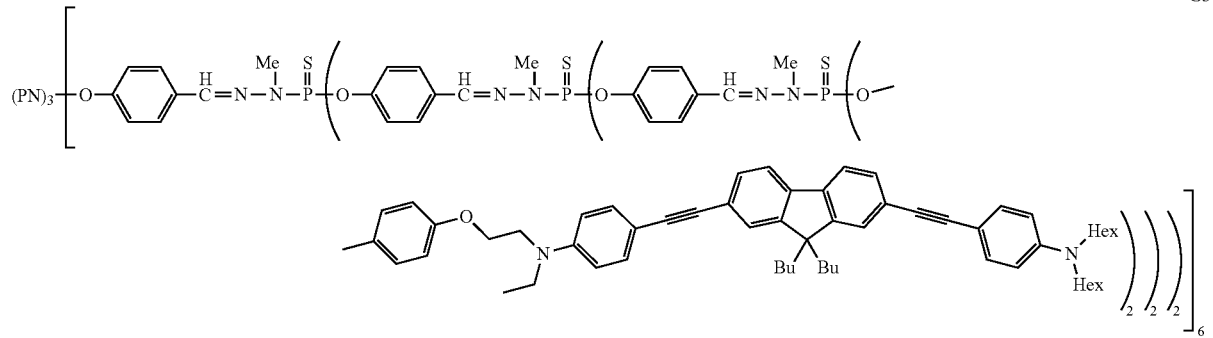

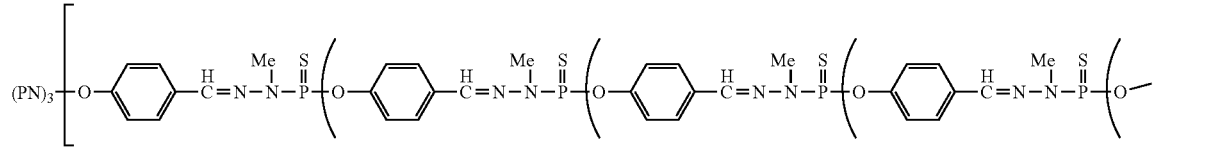

-continued
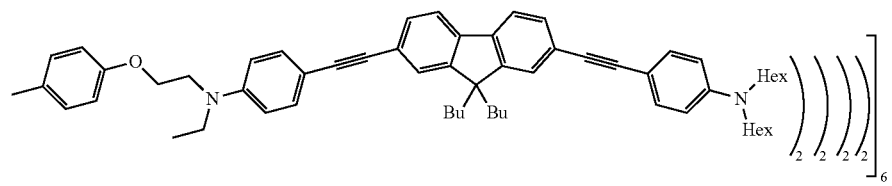
G'2
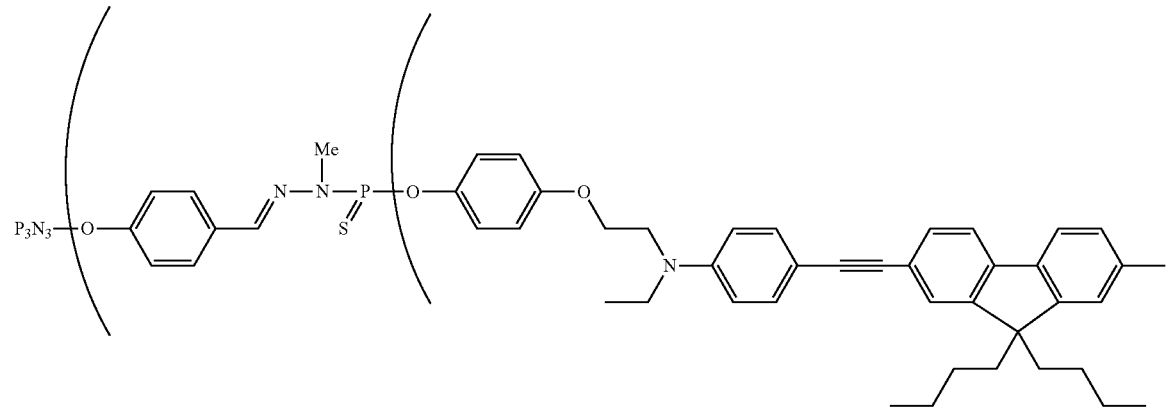
G'3
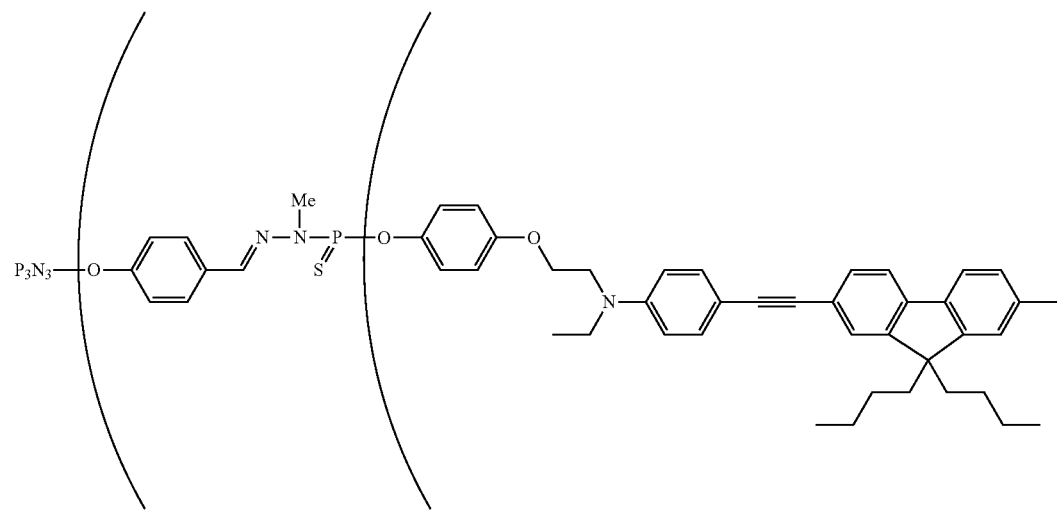

-continued
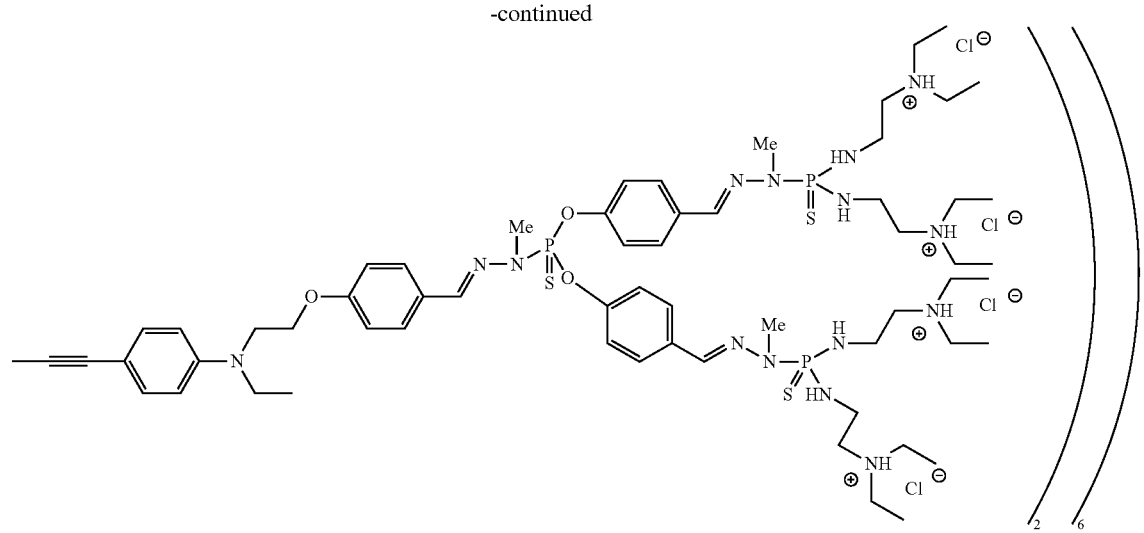
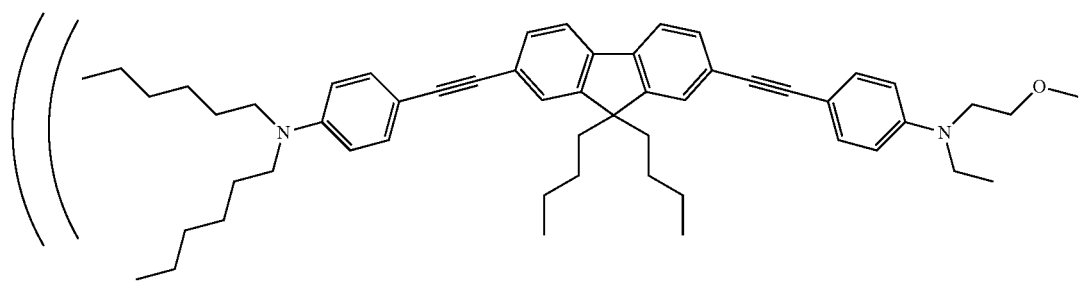
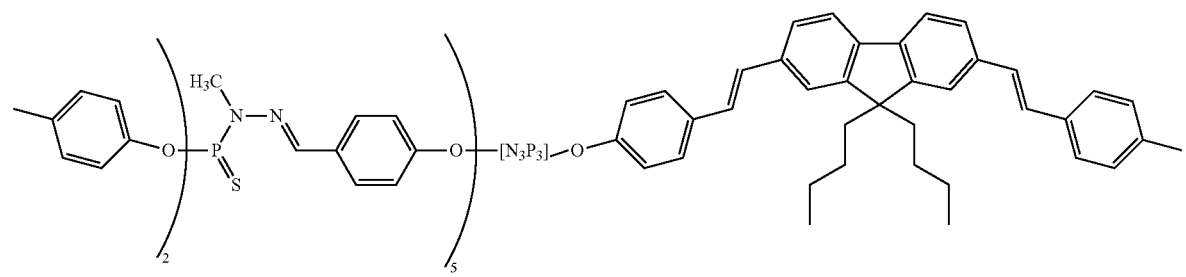
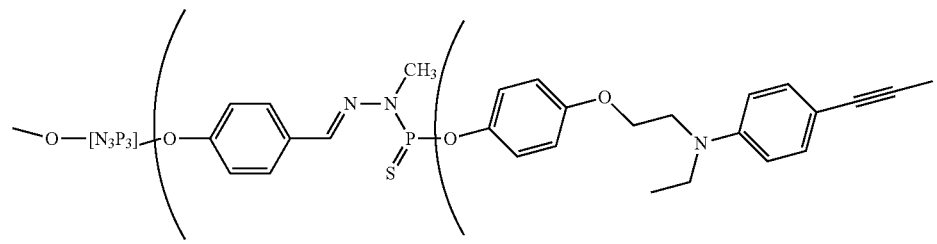
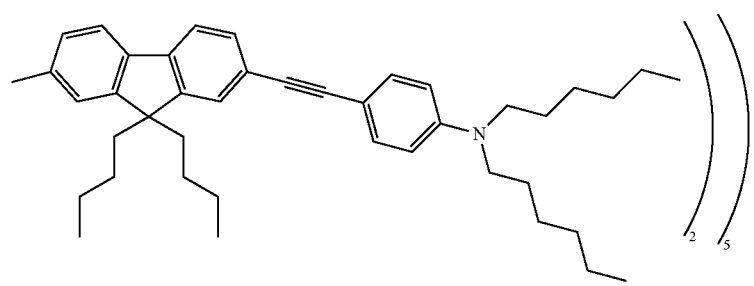

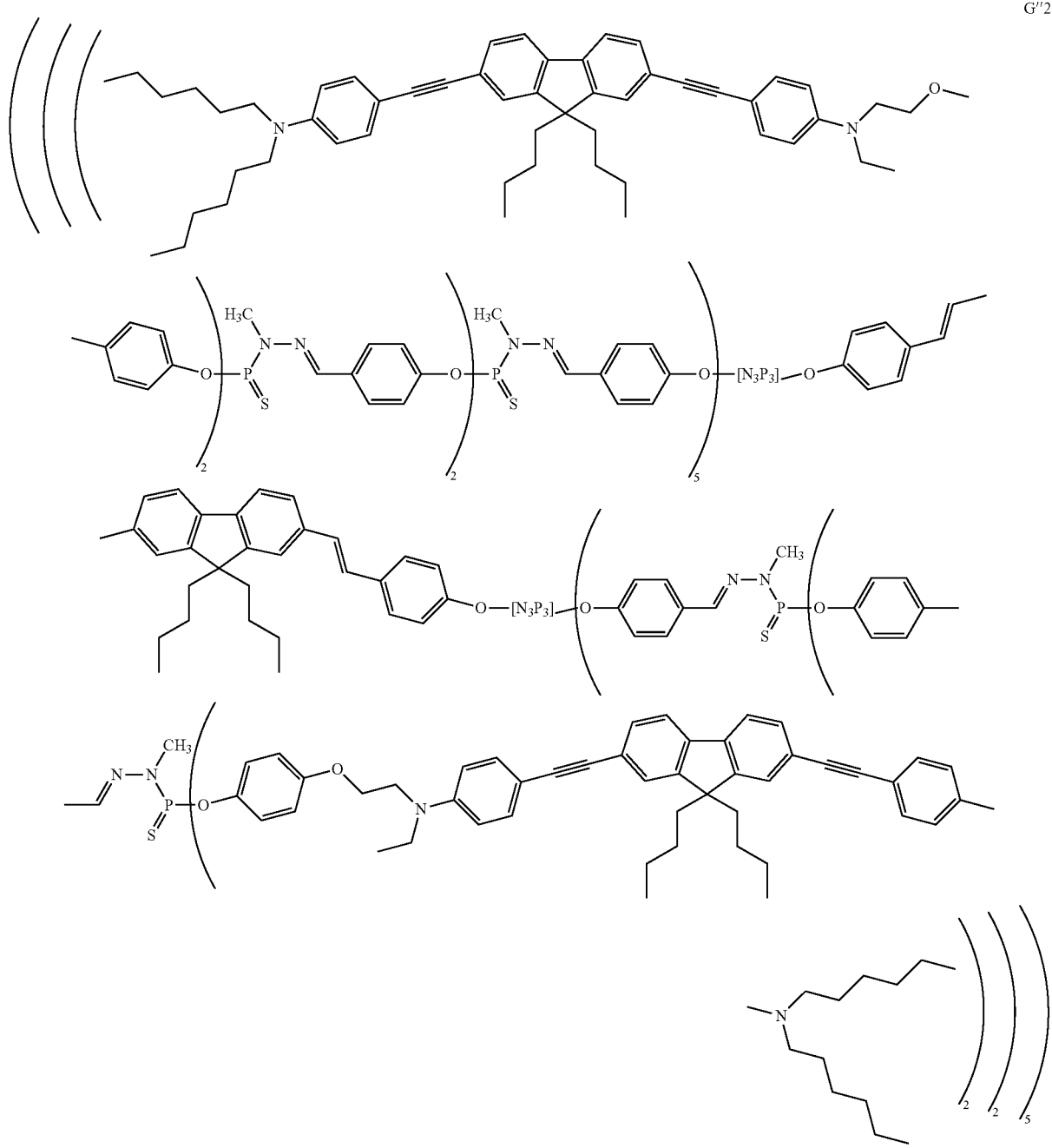

According to another alternative of the invention, the compounds according to the invention can also have two cores with identical or different valences, bound directly to one another or bound to one another by means of a pattern (Y) having two-photon absorption properties.

Also according to an alternative, the compounds according to the invention can have at least two types of patterns (Y, Y') having two-photon absorption properties.

According to such a case, the various types of patterns with two-photon absorption properties can have different wavelength emission properties.

According to a beneficial alternative, the various types of patterns will have two-photon absorption properties with different wavelength emission properties of which the sum leads to the emission of a white light.

The invention also covers any use of such a compound as described above in any process or device implementing a one- or two- or three-photon absorption.

The invention in particular covers any use of such a compound in the context of a biphotonic process or device in particular in the context of a photon imaging process or device.

The invention, as well as the various advantages that it has, can be more easily understood with the following description of non-limiting embodiments provided in reference to the drawings, in which.

According to a first embodiment of the invention, four fluorescent dendrimer chemical compounds were synthesized according to this invention, having respectively 1, 2, 3 and 4 generations with the formulas:

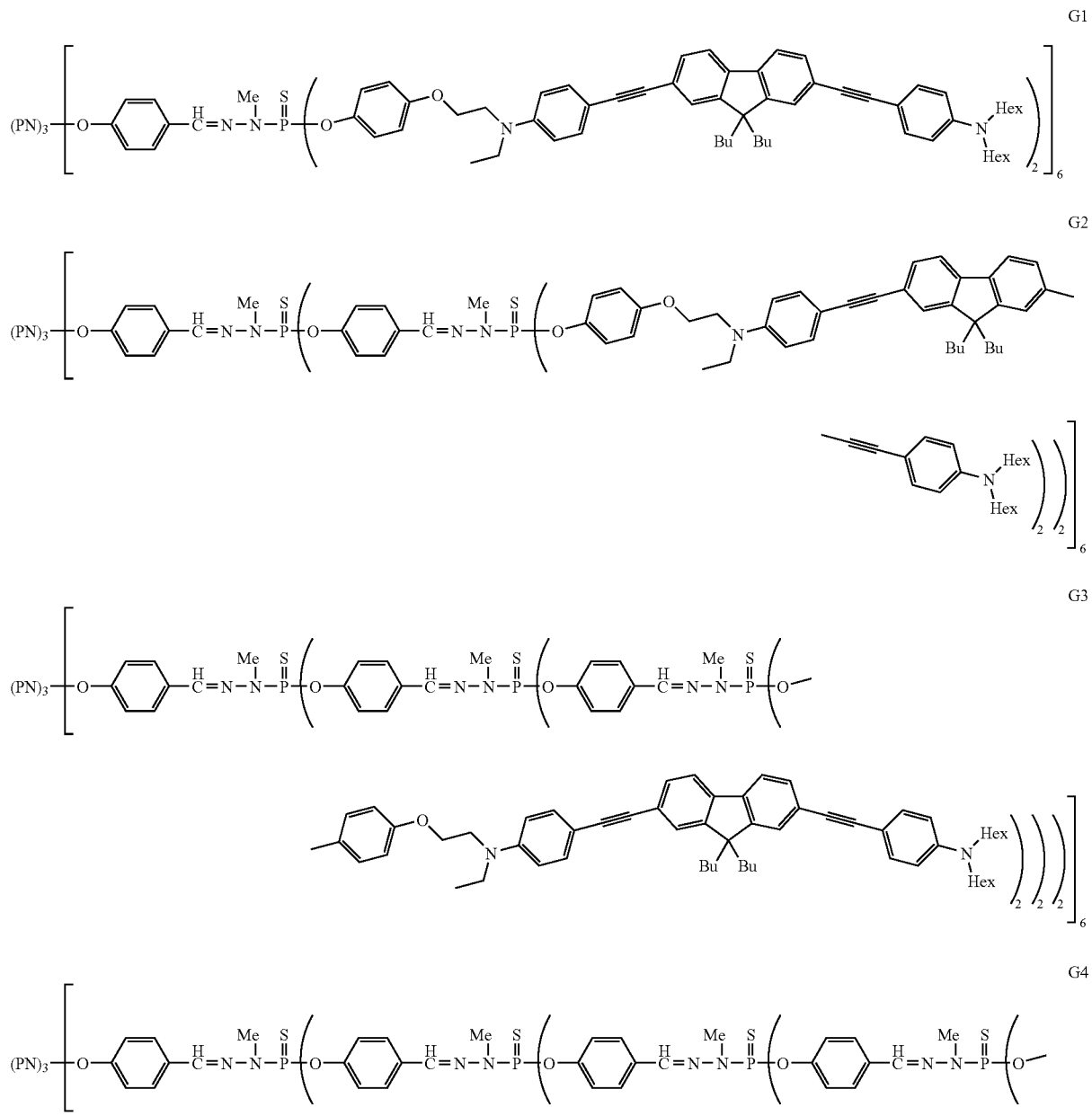

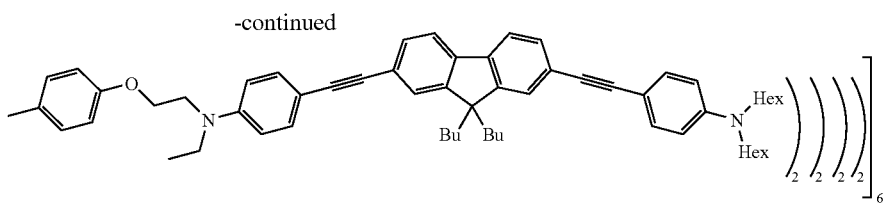

In compound G1, 6 patterns X are directly bound to the core and 12 patterns Y are bound to them. The patterns Y form a generation of the compound.

In compounds G2, G3 and G4, 6 first patterns X are directly bound to the core, the patterns X are bound to these first patterns to form, respectively, 1, 2 and 3 generations of compounds, and patterns Y belong to the "outer" generation of each compound.

These compounds have a core with 6 valences of formula:

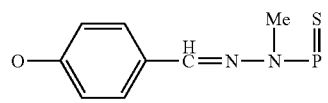

non-chromophoric generation chains in a tree structure around the core (patterns X) of formula:

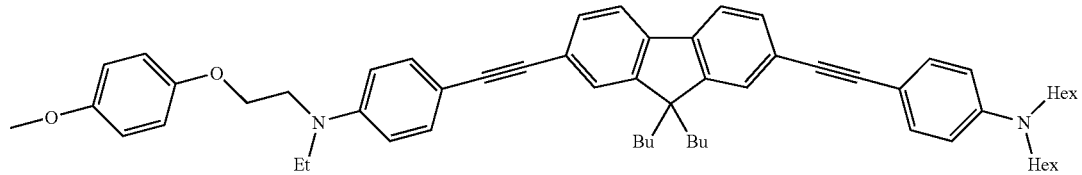

and chromophoric patterns (patterns Y) of formula:

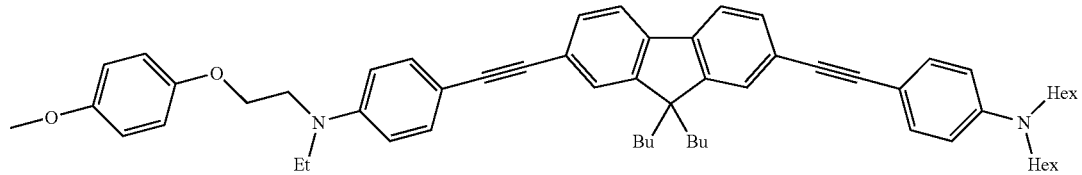

These compounds according to the invention have been produced by reacting dendrimers of formulas 2-G1, 2-G2, 2-G3 and 2-G4, and having the above core and the pattern X:

2-G1

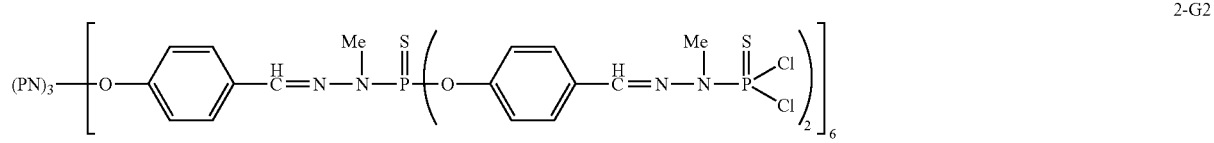

2-G2

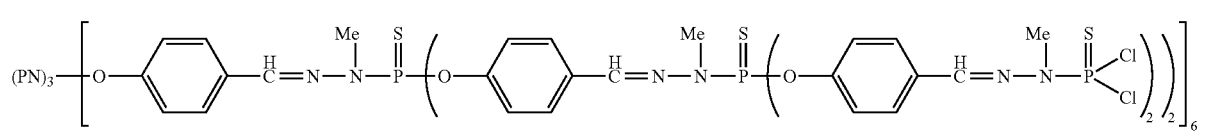

2-G3

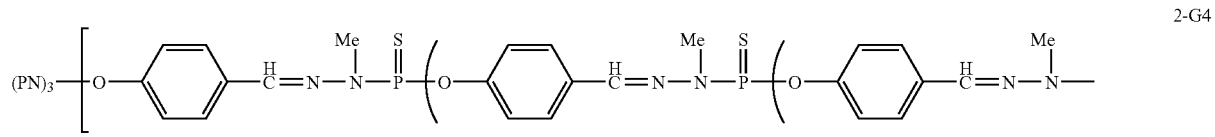

2-G4

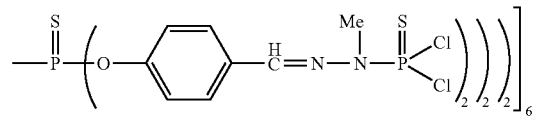

with increasing amounts of a two-photon absorption chromophores of formula 1 having the pattern Y:

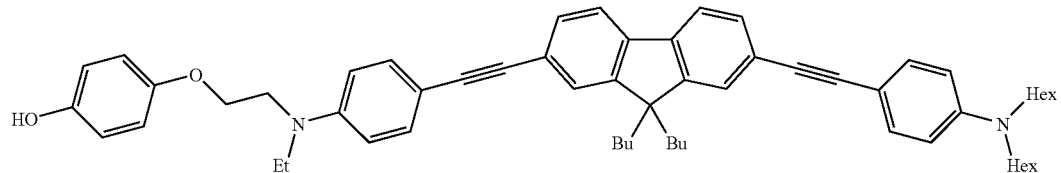

by nucleophile substitution of the terminal P(S)Cl$_2$ groups.

Figure 1:
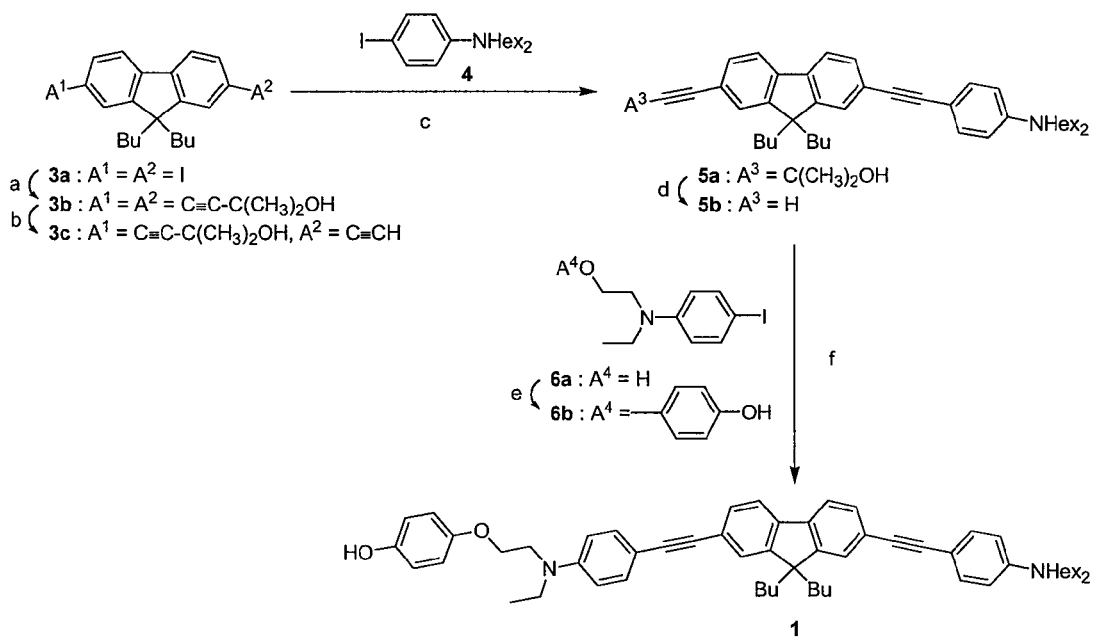
FIG. 1 shows the general diagram of the synthesis a fluorophore intended to form the chromophoric pattern Y of compounds according to the invention.
Figure 2:
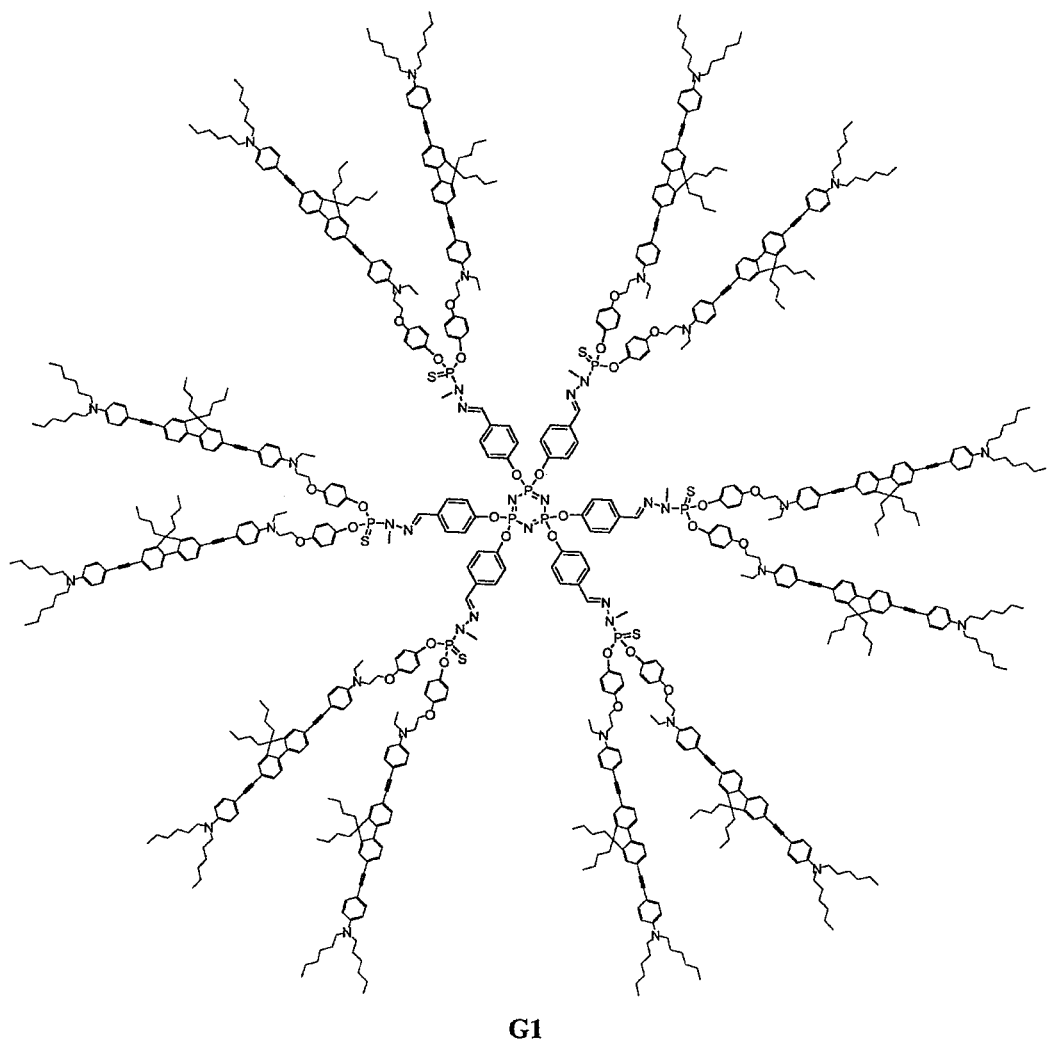
FIGS. 2 to 5 show the developed structures of four compounds G1 to G4 according to the invention.
Figure 3:
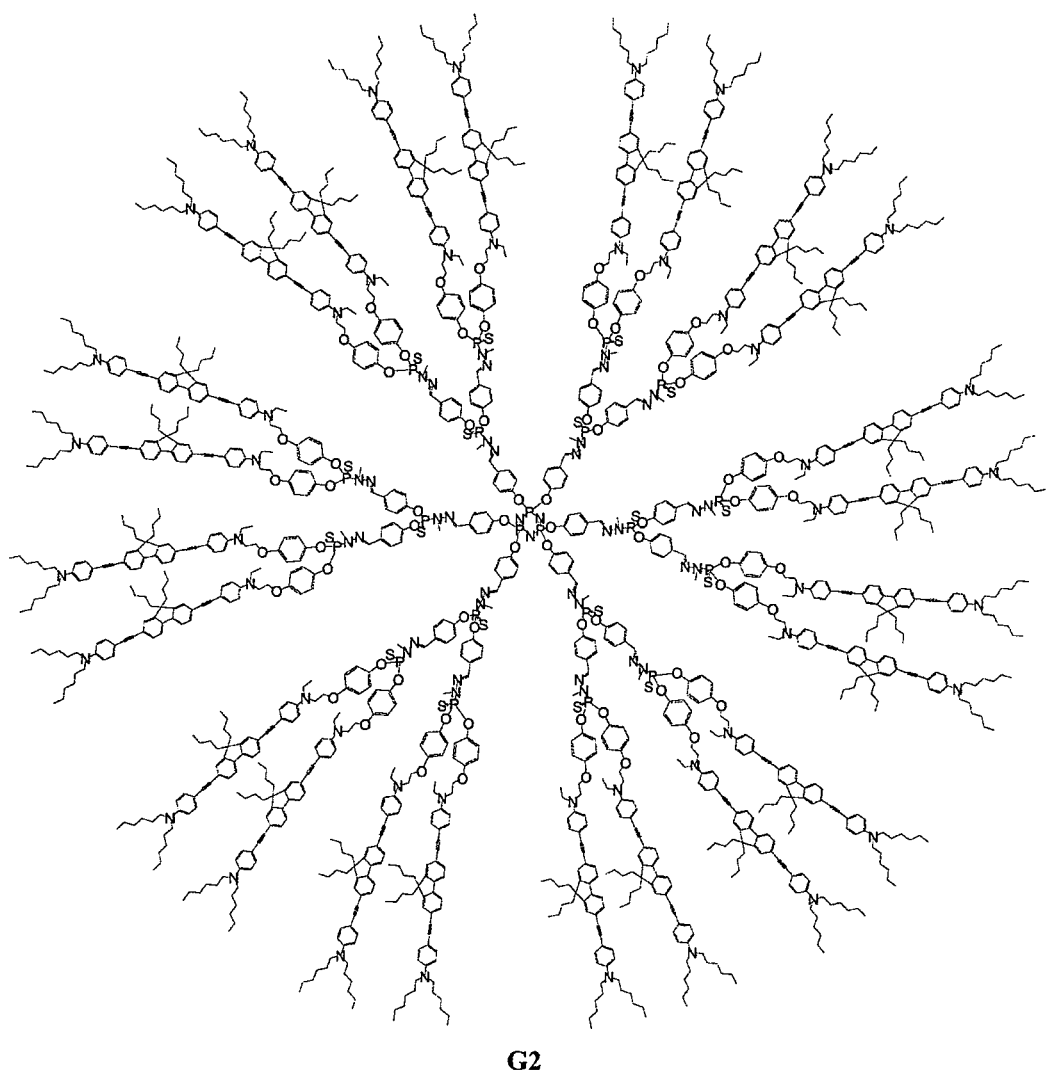
Figure 4:
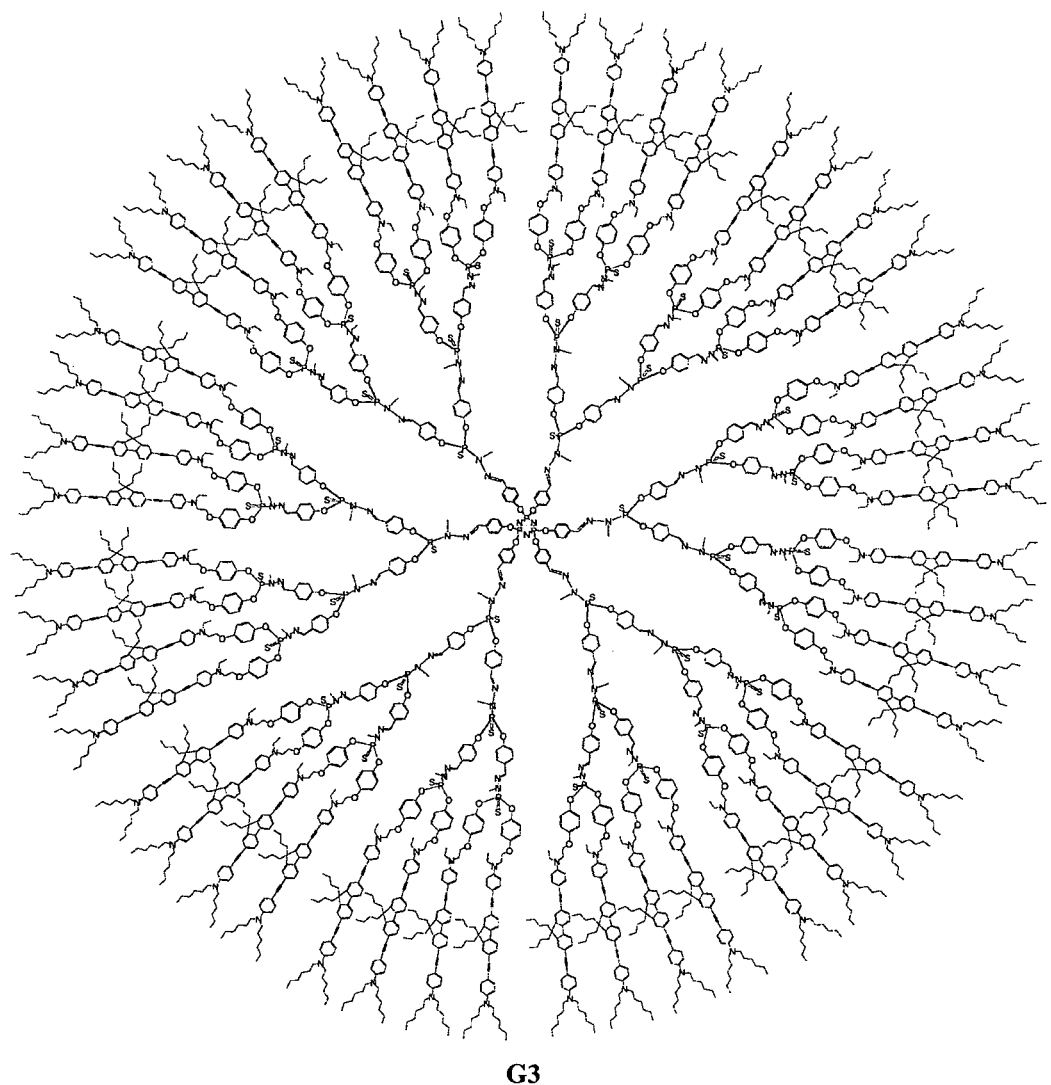
Figure 5:
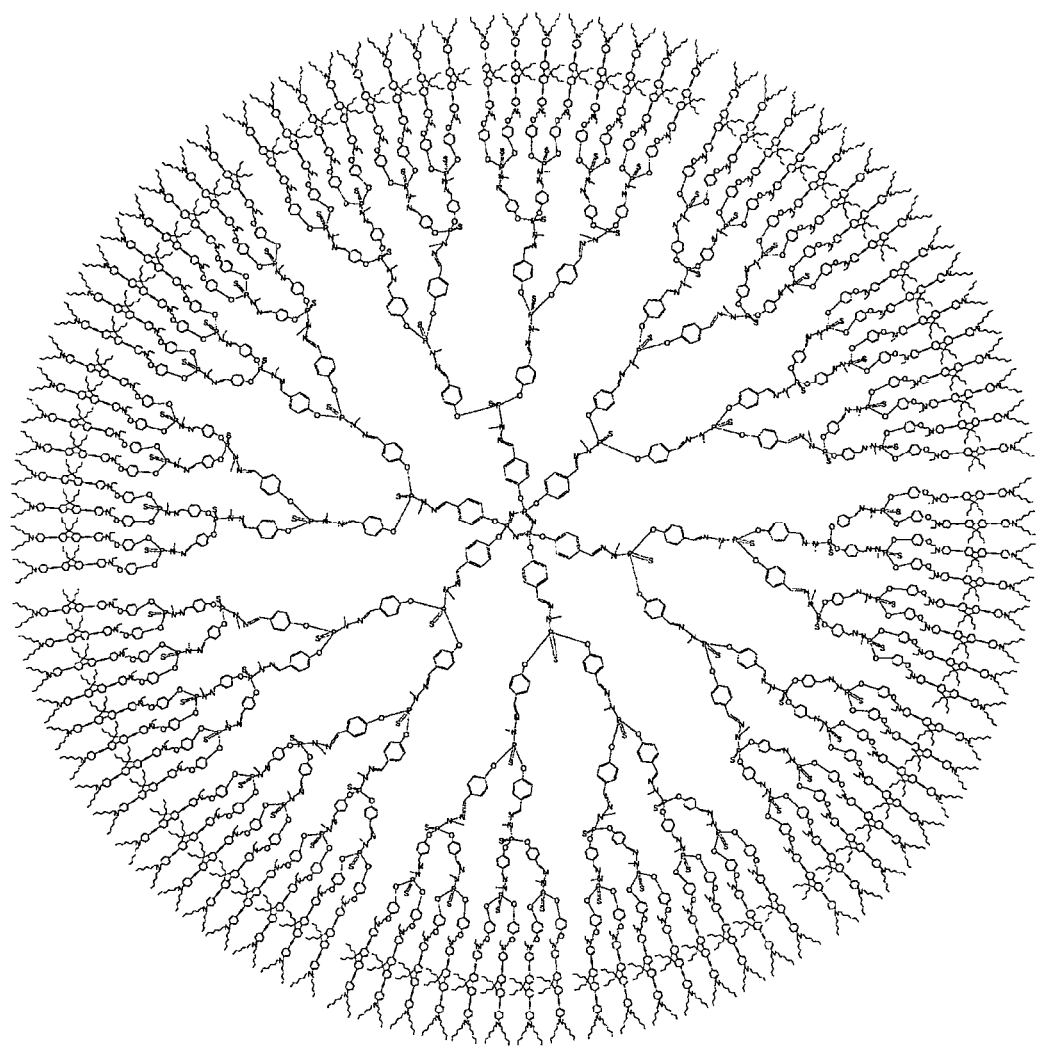

The two-photon absorption chromophores 1 was prepared by the process indicated in FIG. 1.

Dialkyne 3b, obtained from 2,7-diiodo-9,9-dibutyl-9H-fluorene 3a, is deprotected in a controlled manner to produce true alkyne 3c. The Sonogashira coupling of 3c with the iodized derivative 4 leads to compound 5a, of which the deprotection leads to the new true alkyne 5b. This derivative is coupled with a second iodized derivative (6b), bearing a phenol function enabling grafting with the dendrimers 2-G1, 2-G2, 2-G3 and 2-G4.

More specifically, the compounds 3b, 3c, 5a, 5b, 6b and the chromophore 1 were obtained according to the following protocols:

4,4'-(9,9-Dibutyl-9H-fluorene-2,7-diyl)bis(2-methyl-3-butyn-2-ol) (3b)

The air is purged from a solution of 3a (6.00 g, 11.3 mmol) in 37.5 mL of toluene/Et$_3$N (5/1) by argon bubbling for 20 min. Then, CuI (86 mg, 0.45 mmol), Pd(PPh$_3$)$_2$Cl$_2$ (316 mg, 0.45 mmol) and 2-methyl-3-butyn-2-ol (2.84 g, 33.8 mmol) are added, and the mixture is agitated at 40° C. for 16 h. After evaporation of the solvent under reduced pressure, the raw product is purified by silica gel column chromatography (heptane/CH$_2$Cl$_2$ 30:70 then CH$_2$Cl$_2$) to yield 4.37 g (87%) of 4,4'-(9,9-dibutyl-9H-fluorene-2,7-diyl)bis(2-methyl-3-butyn-2-ol).

4-(9,9-Dibutyl-7-ethynyl-9H-fluorene-2-yl)-2-methyl-3-butyn-2-ol (3c)

Soda powder (0.73 g) is added to a solution of 3b (4.02 g, 9.09 mmol) in 50 mL of toluene/z-PrOH (6/1). The mixture is heated in a reverse-flow boiler for 0.5 h. After cooling, the soda is filtered and the solvents are evaporated. The compounds are separated by silica gel column chromatography (heptane/CH$_2$Cl$_2$ 70:30 then 20:80) to yield 0.66 g (22%) of 9,9-dibutyl-2,7-diethynyl-9H-fluorene and 1.54 g (44%) of 3c.

[9,9-Dibutyl-7-[2-[4-(dihexylamino)phenyl]ethynyl]-9H-fluoren-2-yl]-2-methyl-3-butyn-2-ol (5a)

The air is purged from a solution of 3c (1.304 g, 3.39 mmol) and 4 (1.71 g, 4.41 mmol) in 10.8 mL of toluene/Et$_3$N (5/1) by argon bubbling for 20 min. Then, CuI (12.9 mg, 0.068 mmol) and Pd(PPh$_3$)$_2$Cl$_2$ (48 mg, 0.068 mmol) are added, and the mixture is agitated at 40° C. for 3.5 h. The solvent is evaporated under reduced pressure, and the raw product is purified by silica gel column chromatography (heptane/CH$_2$Cl$_2$ 75:25 then 30:70) to yield 817 mg (37%) of 5a.

4-[2-(9,9-Dibutyl-7-ethynyl-9H-fluoren-2-yl)ethynyl]-N,N-dihexylbenzenamine (5b)

Potash powder (0.07 g) is added to a solution of 5a (0.798 g, 1.24 mmol) in 8.75 mL of toluene/i-PrOH (6/1). The mixture is heated in a reverse-flow boiler for 1 h. After cooling, the potash is filtered and the solvents are evaporated. The raw product is purified by silica gel column chromatography (heptane/CH$_2$Cl$_2$ 90:10) to yield 0.632 g (87%) of 5b.

4-[2-[Ethyl-(4-iodophenyl)amino]ethoxy]phenol (6b)

A solution of DEAD (9.00 g, 51.7 mmol) in THF (40 mL) is added drop-by-drop to a solution of 6a (5.00 g, 17.2 mmol), hydroquinone (5.65 g, 51.3 mmol) and triphenylphosphine (13.50 g, 51.5 mmol) in THF (110 mL). The mixture is agitated at 20° C. for 16 h and the solvent is evaporated under reduced pressure. The residue is purified by silica gel column chromatography (CH$_2$Cl$_2$) to yield 3.35 g (51%) of 6b.

4-[2-[[4-[2-[9,9-Dibutyl-7-[2-[4(dihexylamino)phenyl]ethynyl]-9H-fluoren-2-yl]ethynyl]phenyl]ethylamino]ethoxy]phenol (1)

The air is purged from a solution of 5b (155.9 mg, 0.266 mmol) and 6b (132.6 mg, 0.346 mmol) in 1.2 mL of toluene/Et$_3$N (5/1) by argon bubbling for 20 min. Then, CuI (1.0 mg, 0.005 mmol) and Pd(PPh$_3$)$_2$Cl$_2$ (3.7 mg, 0.005 mmol) are added, and the mixture is agitated at 40° C. for 16 h. The solvent is evaporated under reduced pressure, and the raw product is purified by chromatography in a silica gel column (heptane/CH$_2$Cl$_2$ 70:30 then 20:80) to yield 127.9 mg (57%) of 1.

The dendrimers of formula 2-G1, 2-G2, 2-G3 and 2-G4 were prepared according to the protocol described by Launay et al., *Journal of Organometallic Chemistry*, 1997, 529, 51-58.

Solutions of dendrimers of formula 2-G1, 2-G2, 2-G3 and 2-G4 were then placed in contact with increasing amounts of fluorophore of formula 1 in the presence of increasing amounts of $Cs_2CO_3$.

For compound G1, 12 moles of chromophores and 12 moles of $Cs_2CO_3$ were used for one mole of dendrimer.

For compound G2, 24 moles of chromophores and 24 moles of $Cs_2CO_3$ were used for one mole of dendrimer.

For compound G3, 48 moles of chromophores and 48 moles of $Cs_2CO_3$ were used for one mole of dendrimer.

For compound G4, 96 moles of chromophores and 96 moles of $Cs_2CO_3$ were used for one mole of dendrimer.

More specifically, the compounds G1, G2, G3 and G4 were produced according to the following protocol.

Fluorophore 1 (n=1, 270 mg, 320 μmol; n=2, 270 mg, 320 μmol; n=3, 270 mg, 320 μmol; n=4, 135 mg, 160 μmol) and $Cs_2CO_3$ (n=1, 208 mg, 640 μmol; n=2, 208 mg, 640 μmol; n=3, 208 mg, 640 μmol; n=4, 104 mg, 320 μmol are added to a dendrimer solution 2-Gn (n=1, 44 mg, 24 μmol; n=2, 58 mg, 12 μmol; n=3, 70 mg, 6.5 μmol; n=4, 36 mg, 1.6 μmol) (synthesized according to the method described in Launay et al., *J. Organomet Chem.* 1997, 529, 51) in 20 mL of distilled THF. The resulting mixture is agitated at room temperature for one night, filtered and the solvent is evaporated. The raw product is purified by column chromatography ($SiO_2$; $CHCl_3$/Hexane: 90:10).

Compounds according to this invention with 12, 24, 48 and 96 chromophoric patterns forming the outer layer were thus obtained.

The formulas developed for these compounds are provided in FIGS. 2, 3, 4 and 5.

The photophysical data of fluorophore 1 and of compounds G1, G2, G3 and G4 in toluene were evaluated. The results are provided in table 1 below.

Figure 6:
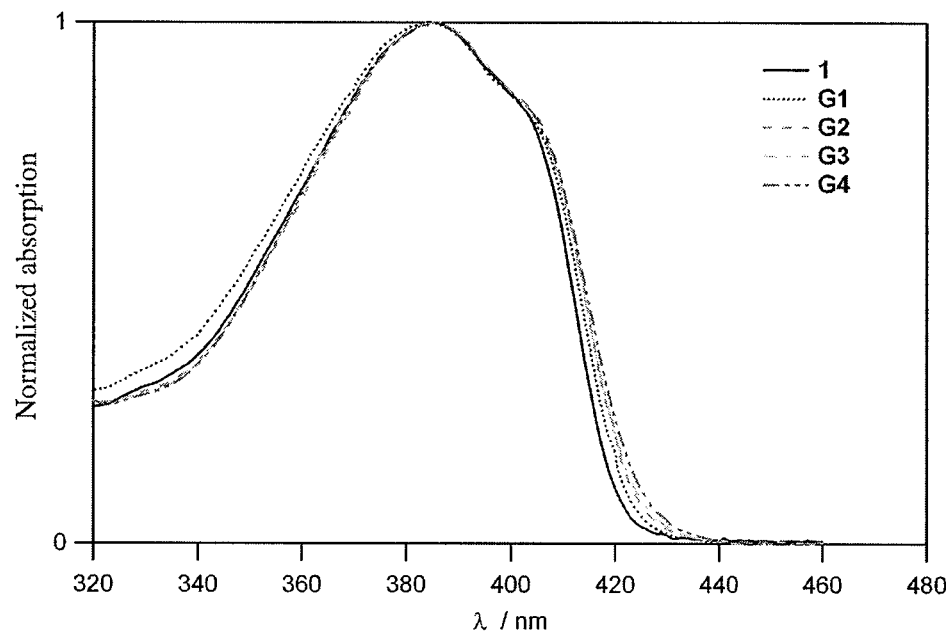
FIGS. 6 and 7 show the absorption and emission spectra, in toluene, of this fluorophore and of these four compounds according to the invention.
Figure 7:
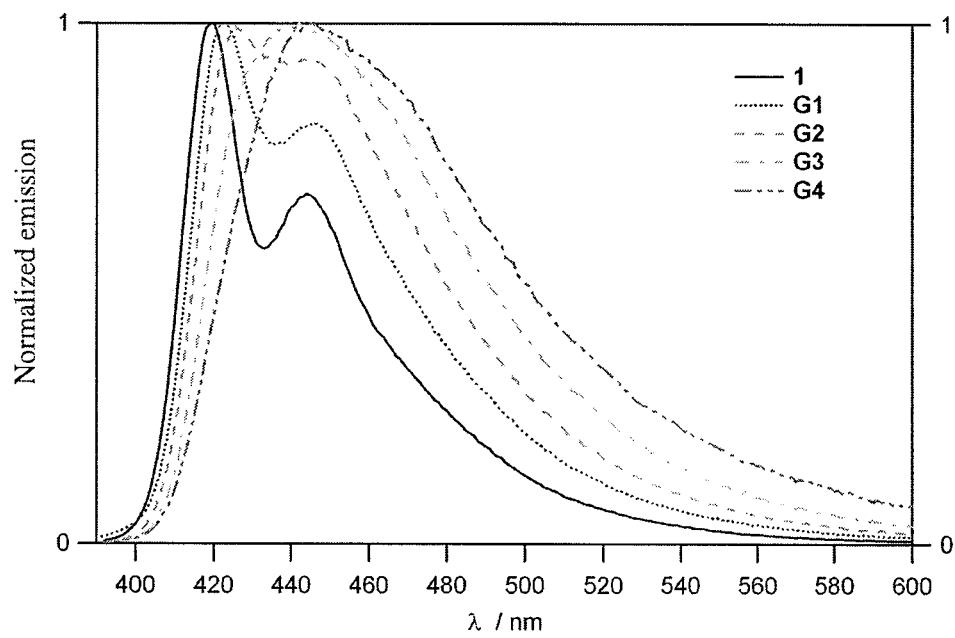

The compounds according to this invention have a photon absorption in the near UV. A quasi-linear increase in the molar extinction coefficient with the number of chromophores is observed. The absorption and emission spectra in toluene are provided in FIGS. 6 and 7.

Advantageously, the various dendrimer compounds maintain high fluorescent quantum efficiencies ($\phi$), in spite of the large number of chromophores concentrated in such a reduced volume. This point is essential for obtaining high brightness.

Figure 8:
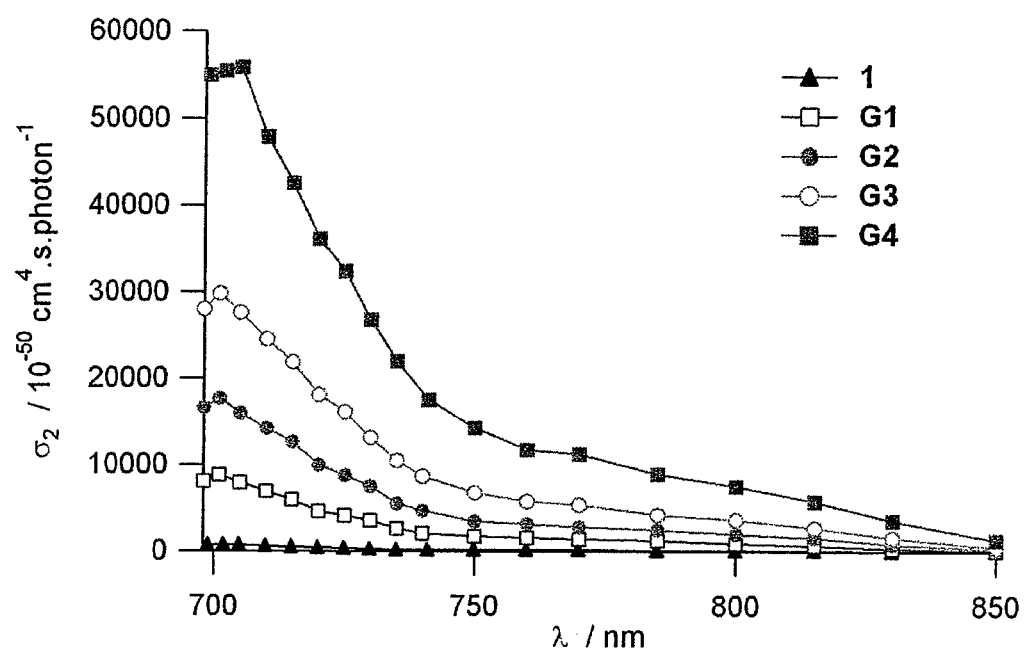
FIG. 8 shows the two-photon absorption spectra in toluene of this fluorophore and of these four compounds according to the invention, determined by TPEF measurements using a titanium-sapphire laser with femtosecond pulses.

The TPA spectra of these compounds G1, G2, G3 and G4, as well as of the chromophore 1, were determined by measuring the TPEF, using a femtosecond pulse laser in toluene. The two-photon absorption spectra are given in FIG. 8.

An increase in the effective two-photon absorption cross-sections is observed with the increase in the number of generations of the dendrimer. In particular, a quasi-linear increase is observed with the increase in the number of chromophores leading to very high effective TPA cross-section values $\sigma_2$ for the dendrimers. The maximum effective TPA cross-section value obtained for dendrimer G4 (55900 GM at 705 nm) is entirely comparable to the effective TPA cross-sections obtained for one of the best quantum dots (Larson et al.).

The compound G4 according to this invention has a diameter that can be estimated at around 8 nm (the quantum dots have a diameter of up to 6 nm without the polymer encapsulating them).

Figure 9:
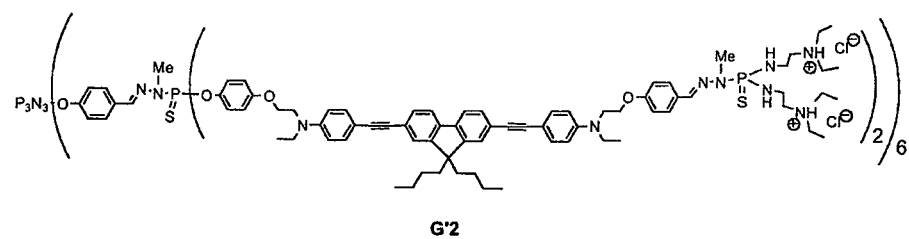
FIGS. 9 and 10 show the formula of two other compounds G'2 and G'3 according to this invention.
Figure 10:
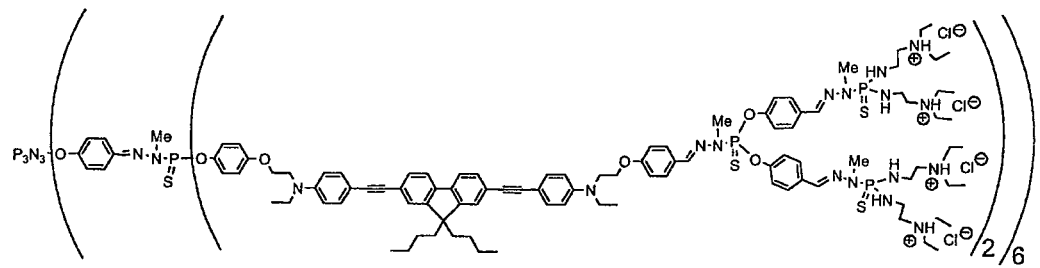

In a second embodiment of the invention, fluorescent dendrimer chemical compounds G'2 and G'3 according to the invention and having the formulas shown in FIGS. 9 and 10 were obtained.

These dendrimer compounds respectively have 2 and 3 generations, namely, from the core:

patterns X as described above in reference to the first embodiment,

TABLE 1

| | Number of fluorophores | $\lambda_{abs}$ (nm) | $\epsilon$ ($M^{-1} \cdot cm^{-1}$) | $\lambda_{em}$ (nm) | $\phi^a$ | $\tau$ $(ns)^b$ | $r^c$ | $\lambda_{ADP}$(max) (nm) | $\sigma_2$ at $\lambda_{TPA}$(max) $(GM)^d$ |
|---|---|---|---|---|---|---|---|---|---|
| 1 | 1 | 386 | 84 900 | 420, 444 | 0.83 | 0.67 | 0.178 | 702 | 765 |
| G1 | 12 | 385 | 1 004 000 | 423, 446 | 0.75 | 0.71 | 0.032 | 701 | 8880 |
| G2 | 24 | 386 | 2 035 000 | 426, 445 | 0.71 | 0.69 | 0.019 | 701 | 17700 |
| G3 | 48 | 386 | 3 785 000 | 441 | 0.62 | 0.71 | 0.013 | 701 | 29800 |
| G4 | 96 | 386 | 7 101 000 | 445 | 0.48 | 0.66 | 0.012 | 705 | 55900 |

[a] Fluorescence quantum efficiency in toluene determined with respect to fluorescein in NaOH 0.1 N.
[b] Experimental fluorescence lifetime.
[c] Stationary fluorescence anisotropy.
[d] 1 GM = $10^{-50}$ $cm^4 \cdot s \cdot photon^{-1}$.

chromophoric patterns Y' of formula,

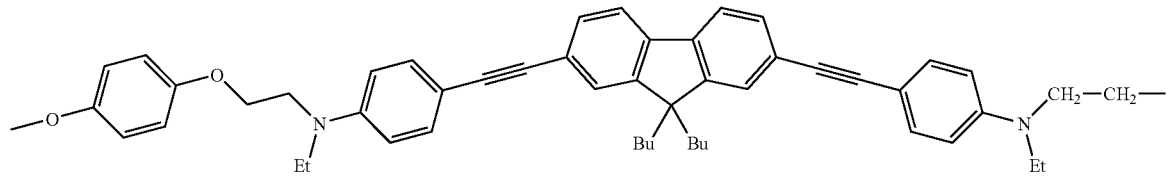

new patterns X, and finally terminal ammonium groupings capable of conferring water-solubility on the compound.

The presence of patterns X between the chromophoric patterns Y' and the terminal ammonium groupings provides the benefit of forming a protective layer making it possible to isolate the chromophoric patterns from the external environment.

The compound G'2 was produced as follows.

Figure 11:
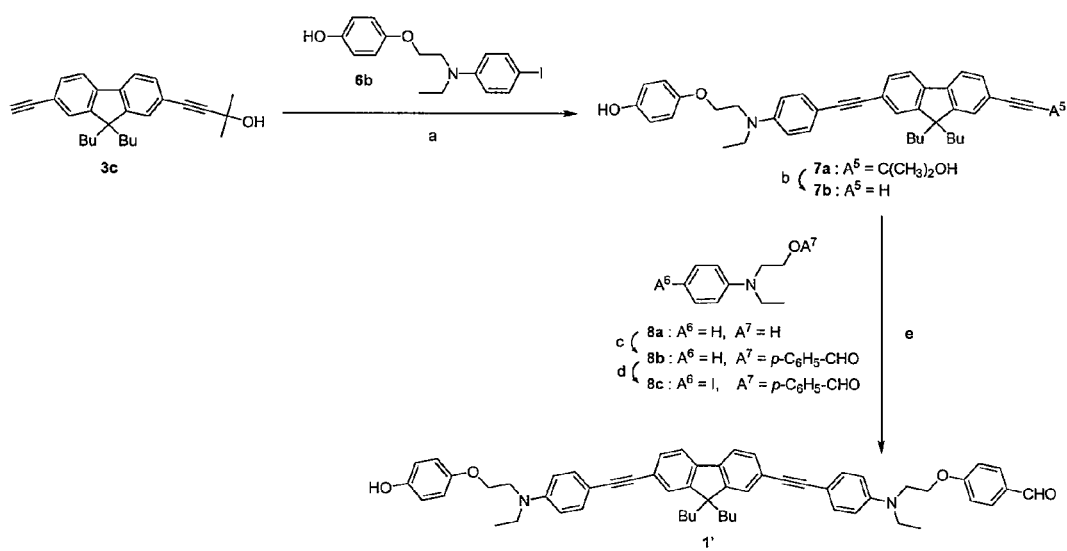
FIG. 11 shows the general diagram of the synthesis of a fluorophore intended to form the chromophoric pattern Y of these two other compounds.

The two-photon absorption chromophores 1', comprising two grafting functions at its ends, was prepared by the process indicated in FIG. 11.

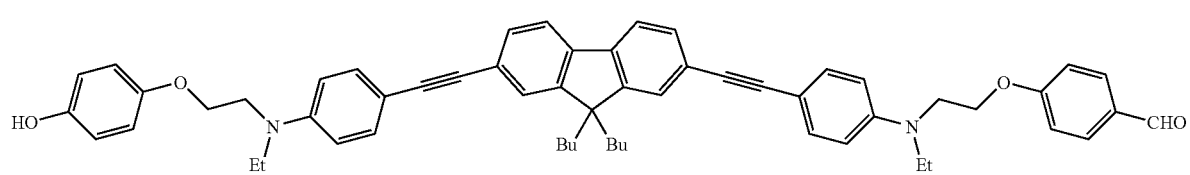

The Sonogashira coupling of the true alkyne 3c with the iodized derivative 6b resulted in the compound 7a, of which the deprotection led to the new true alkyne 7b. This derivative is coupled with a second iodized derivative (8c, obtained in two steps from the commercial compound 8a) and bearing an aldehyde function.

Figure 12:
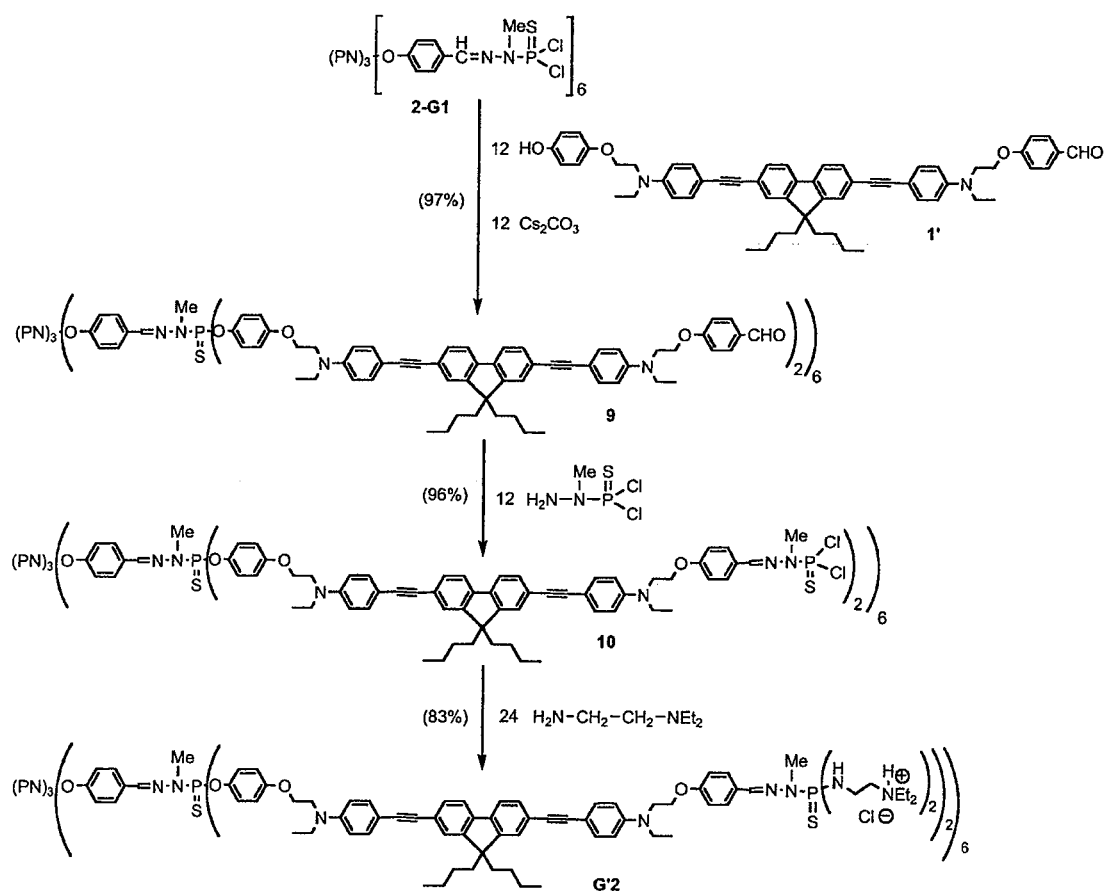
FIG. 12 shows the general diagram of the synthesis of the compound G'2.

As indicated in FIG. 12, the reaction of the first-generation dendrimer 2-G1 (synthesized according to the method described in Launay et al., *J. Organomet Chem.* 1997, 529, 51) with 12 equivalents of the chromophore 1' and 12 equivalents of $Cs_2CO_3$ results in the dendrimer 9, with which 12 equivalents of dichlorophosphonomethyl hydrazide ($H_2NNMeP(S)Cl_2$) are reacted, to obtain the dendrimer 10 of generation 2. Finally, the latter is reacted with 24 equivalents of N,N-diethylethylenediamine ($H_2NCH_2CH_2NEt_2$), to produce the dendrimer G'2, which has 24 ammonium functions at the surface.

More specifically, the compounds 9, 10 and G'2 were obtained according to the following protocols.

Compound 9: Fluorophore (90 mg, 105 µmol) and $Cs_2CO_3$ (68.5 mg, 210 µmol) are added to a first-generation dendrimer solution (16.1 mg, 8.8 µmol), (synthesized according to the method described in Launay et al., *J. Organomet Chem.* 1997, 529, 51), in 20 mL of THF. The resulting mixture is agitated for one night at room temperature, filtered, then evaporated until dry. The raw product is purified by silica column chromatography (eluent: $CH_2Cl_2$/Hexane: 98:2) and makes it possible to isolate 99 mg (97%) of first-generation dendrimer with a fluorophore surface.

Compound 10: A solution of dichlorophosphonom ethyl hydrazide ($H_2NNMeP(S)Cl_2$) (16.7 mg, 93 µmol) in $CHCl_3$ is added to a dendrimer solution (90 mg, 7.7 µmol) in 20 mL of THF, at room temperature. The resulting solution is agitated for one night at room temperature, then the solution is concentrated, precipitated in pentane, and the mixture is filtered. The powder is then washed with a solution of pentane/ether (1:2) to produce 101 mg (96%) of generation 2 compound.

Compound G'2: A solution of N,N-Diethylethylenediamine (5.5 mg, 47.9 µmol) is added to a solution of dendrimers with $P(S)Cl_2$ ends (27 mg, 1.9 µmol) in 10 mL of THF, under strong agitation. After one night under agitation at room temperature, the precipitate is eliminated by filtration and the solvent is evaporated. The powder thus obtained is washed with THF and dried under vacuum to obtain 27 mg (83%) of generation 2 dendrimer.

Figure 13:
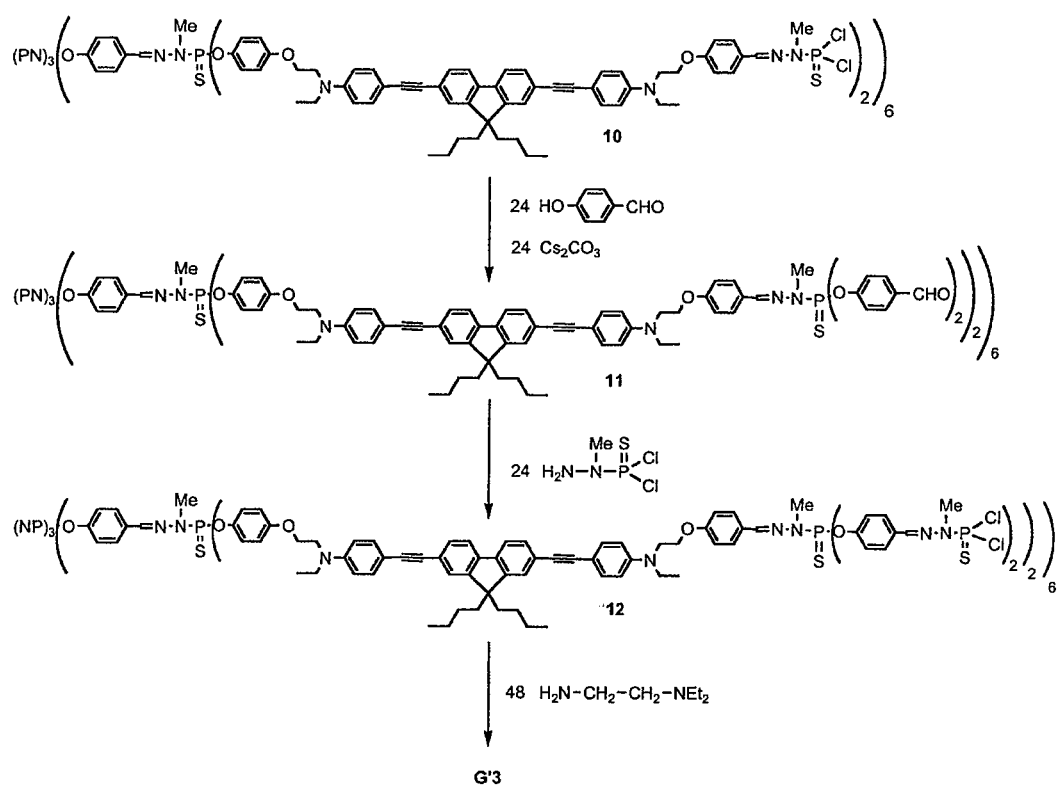
FIG. 13 shows the general diagram of the synthesis of the compound G'3.

Compound G'3 was prepared, as described in FIG. 13, from the dendrimer 10 of generation 2, on which 24 equivalents of 4-hydroxybenzaldehyde and 24 equivalents of $Cs_2CO_3$ were reacted to produce dendrimer 11 with 24 terminal aldehyde functions. The reaction of 11 with 24 dichlorophosphonomethyl hydrazide ($H_2NNMeP(S)Cl_2$) equivalents makes it possible to obtain the dendrimer 12 of generation 3. Finally, the latter is reacted with 48 equivalents of N,N-diethylethylenediamine ($H_2NCH_2CH_2NEt_2$), to produce dendrimer G'3, which has 48 ammonium functions at the surface.

More specifically compounds 11 and G'3 were produced according to the following protocols.

Compound 11: 4-hydroxybenzaldehyde (9.8 mg, 7.9 µmol) and $Cs_2CO_3$ (52.1 mg, 160 µmol) are added to a solution of dendrimers with $P(S)Cl_2$ ends (45 mg, 3.3 µmol) in 20 of mL THF. The resulting heterogeneous solution is agitated for one night at room temperature. The solvent is evaporated and the powder is dissolved in chloroform. The organic phase is washed with brine, dried on $Na_2SO_4$, filtered and evaporated until dry. The resulting powder is washed twice with ether to produce 49 mg (95%) of the dendrimer of generation 2.

Compound G'3: A solution of dichlorophosphonomethyl hydrazide ($H_2NNMeP(S)Cl_2$) (12.4 mg, 69.3 µmol) in $CHCl_3$ is added to a solution a generation 2 dendrimers with aldehyde ends (45 mg, 2.9 µmol) in 20 mL of THF, at room temperature. The resulting solution is agitated for 25 minutes, then concentrated, precipitated in pentane, and the mixture is filtered. The powder is then washed with a pentane/ether solution (1:2) to produce 54 mg (96%) of the dendrimer of generation 3.

In a third embodiment of the invention, fluorescent dendrimer chemical compounds G"1 and G"2 were produced according to the invention, with the formulas:
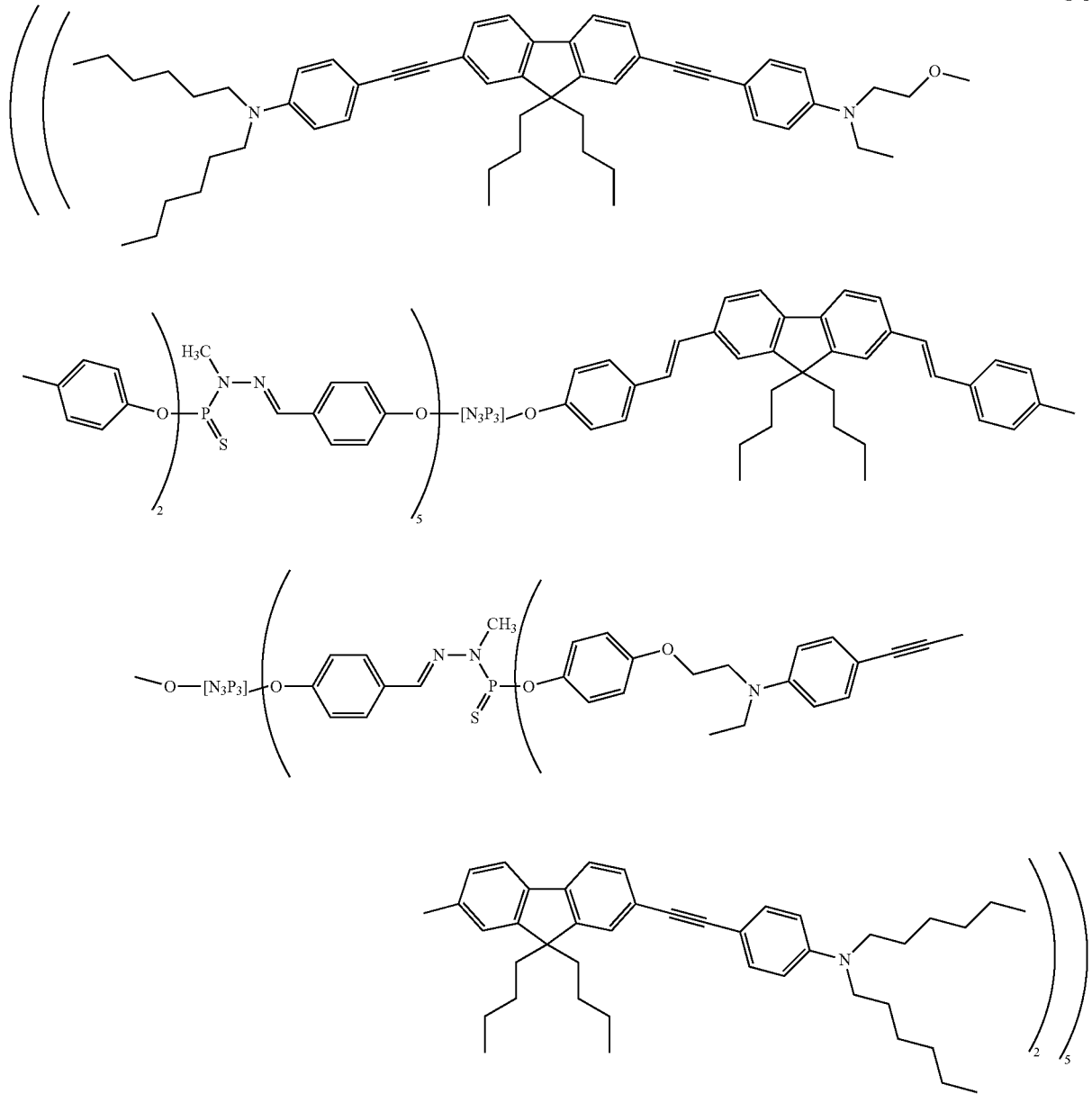
G"1
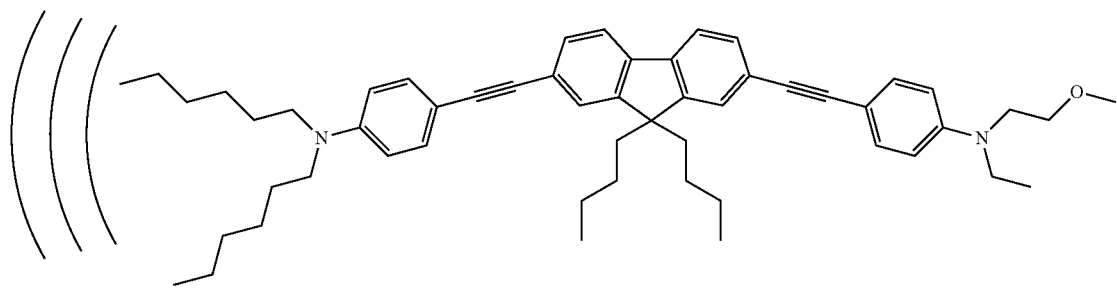
G"2

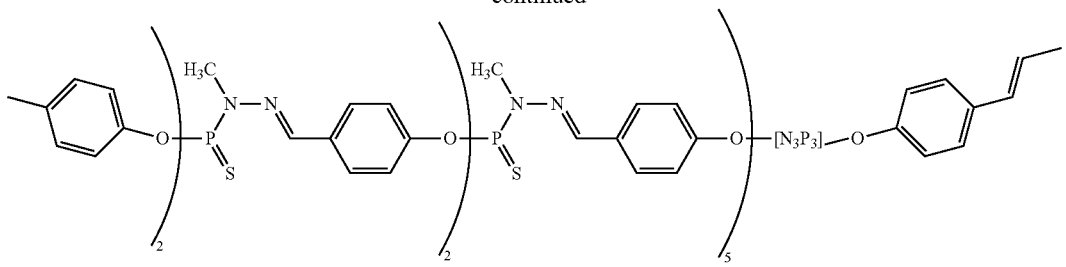

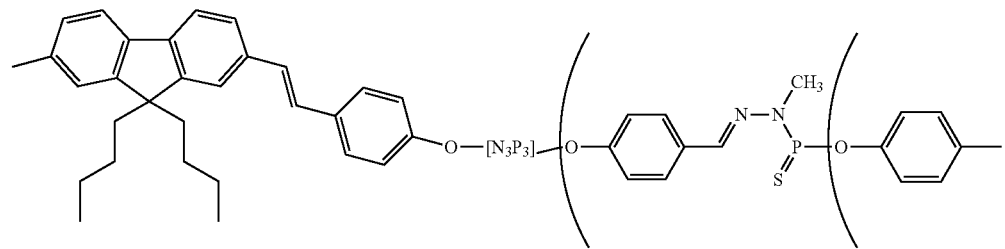

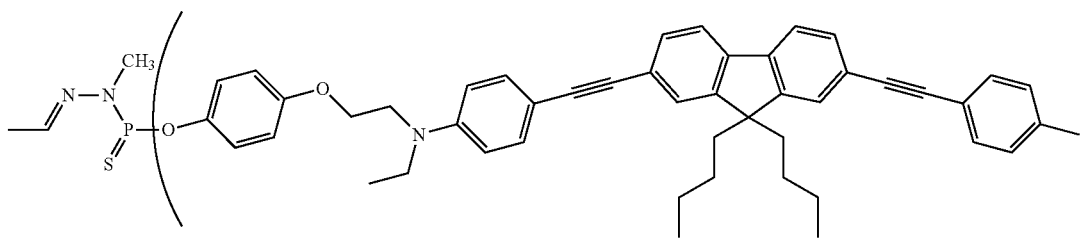

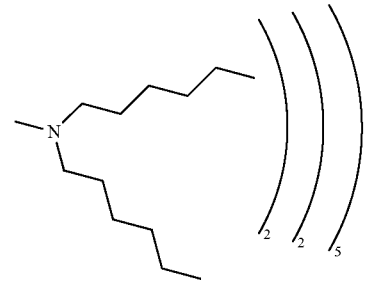

These dendrimer compounds respectively have 1 and 2 generations.

In compound G"1, 10 patterns X are directly bound to the core and 20 patterns Y are bound to them. The patterns Y form a generation of the compound.

In compound G"2, 10 first patterns X are directly bound to the core, and 20 patterns are bound to these first patterns to form, respectively, 1 generation of the compound and 40 patterns Y belonging to the "outer" generation of each compound.

These compounds have a core with 10 valences of formula:

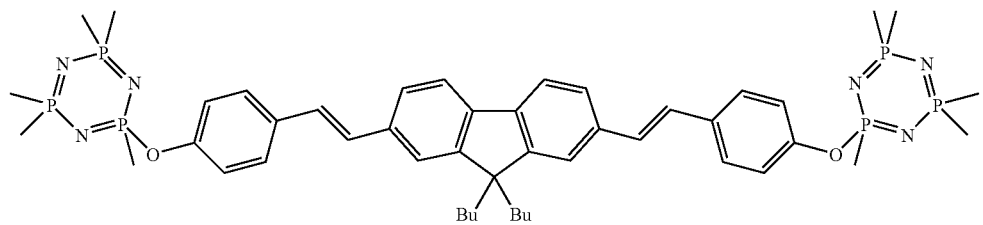

non-chromophoric generation chains in a tree structure around the core (patterns X) of formula:

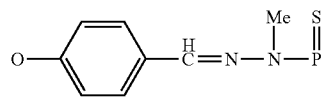

and chromophoric patterns (patterns Y) of formula:

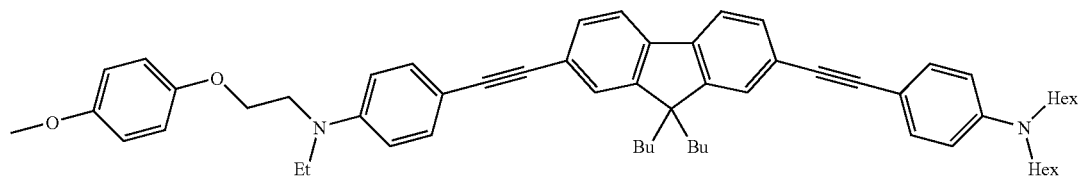

Figure 14:
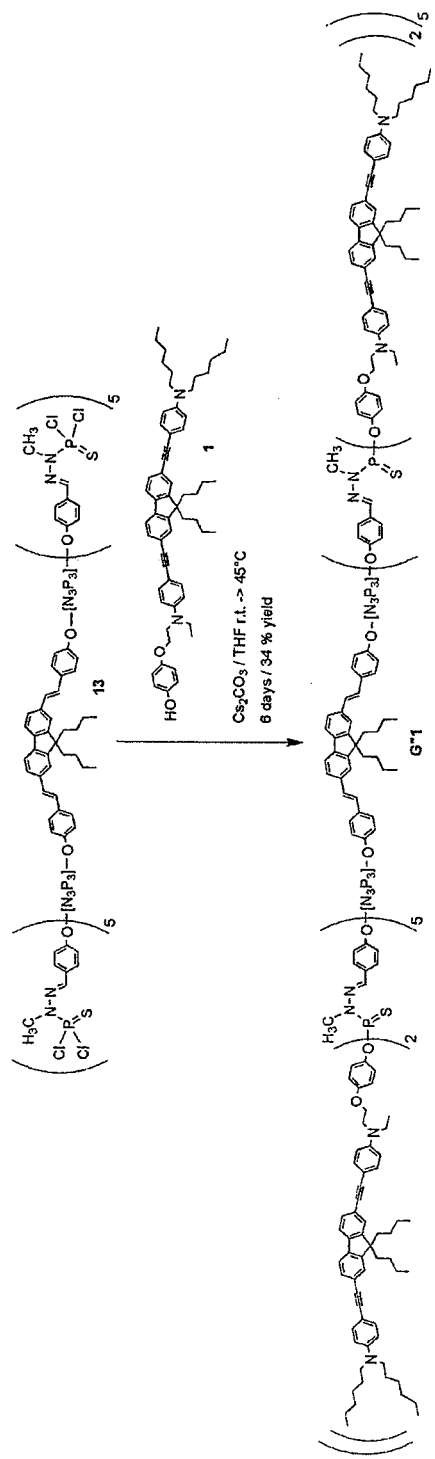
FIG. 14 shows the general diagram of the synthesis of the compound G"1 according to this invention.
Figure 15:
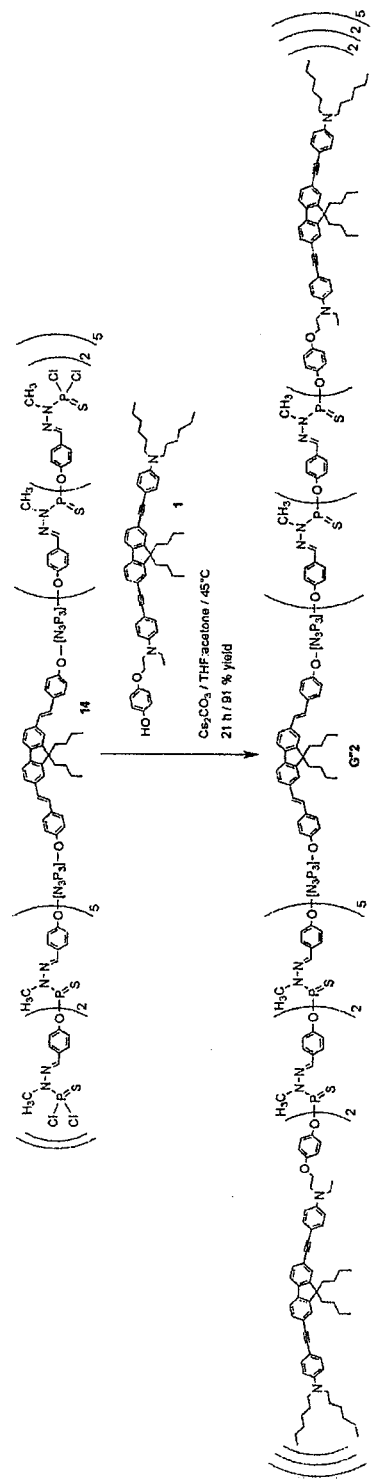
FIG. 15 shows the general diagram of the synthesis of the compound G"2 according to this invention.

As indicated in FIGS. 14 and 15, these two compounds according to the invention were synthesized by reacting dendrimers of formulas 13 and 14 (prepared according to the method described in Krishna et al., Angew. Chem. Int. Ed. 2006, 45, 4645) with increasing amounts of two-photon absorption chromophores of formula 1 by nucleophile substitution of the terminal $P(S)Cl_2$ groups.

More specifically, the compounds G"1 and G"2 were produced according to the following protocol.

Compound G"1: Dendrimer 13 (0.010 g, 2.83 μmol), fluorophore 1 (0.049 g, 58.2 μmol), caesium carbonate (0.038, 113.94 μmol) and tetrahydrofurane (7 mL) are placed in a 50-mL Schlenck, and agitated at room temperature for 15 h, then at 45° C. for 6 days. The salts are filtered and the solvent is evaporated when the reaction is terminated (followed by NMR $^{31}$P). The product is purified by column chromatography (Florisil®, $CHCl_3$ at $THF:CH_3OH$ as eluent mixtures), then by washing with diethylether, to produce dendrimer G"1 (0.0191 g, 34% efficiency).

Compound G"2: Dendrimer 14 (0.078 g, 0.91 μmol), fluorophore 1 (0.031 g, 36.48 μmol), caesium carbonate (0.026 g, 78.09 μmol) and an acetone:THF mixture 1:1 (6 mL) are placed in a 50-mL Schlenck, and agitated at 45° C. for 21 h. The salts are filtered and the solvent is evaporated when the reaction is terminated (followed by NMR $^{31}$P). The orange solid obtained is washed repeatedly with diethylether until there is no more trace of fluorophore 1. The solid is then placed in dichloromethane, filtered and the solvent is evaporated to produce dendrimer G"2 (0.034 g, 91% efficiency).

The photophysical data on compounds G"1 and G"2 in toluene was evaluated. The results are provided in table 2 below.

TABLE 2

| | Number of fluorophores | $\lambda_{abs}$/ nm | r/ ($M^{-1}$ $cm^{-1}$) | $\lambda_{em}$/ nm | $\Phi^a$ | $\tau$/ns$^b$ | $\sigma_2$ at $\lambda_{TPA}$(max)/ GM$^c$ |
|---|---|---|---|---|---|---|---|
| G"1 | 20 | 382 | 1 537 000 | 444 | 0.11 | 0.71 | 14 300 |
| G"2 | 40 | 384 | 3 000 000 | 445 | 0.26 | 0.65 | 32 800 |

$^a$Fluorescence quantum efficiency in toluene determined with respect to fluorescein in NaOH 0.1 N.
$^b$Lifetime of experimental fluorescence.
$^c$1 GM = $10^{-50}$ $cm^4s \cdot photon^{-1}$.

Figure 16:
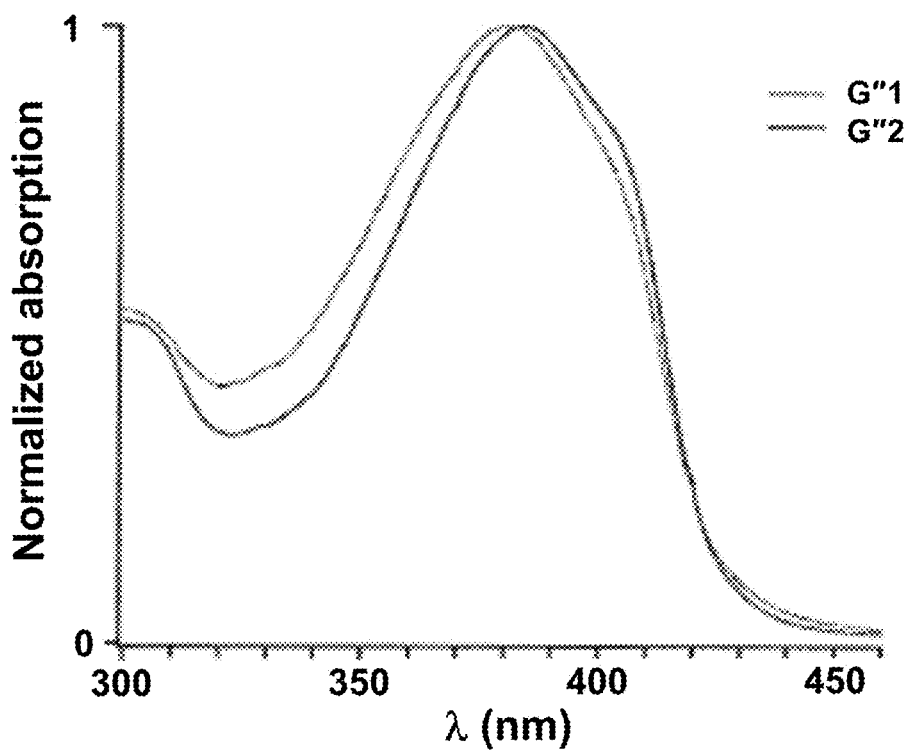
FIGS. 16 and 17 show the absorption and emission spectra in toluene of compounds G"1 and G"2.
Figure 17:
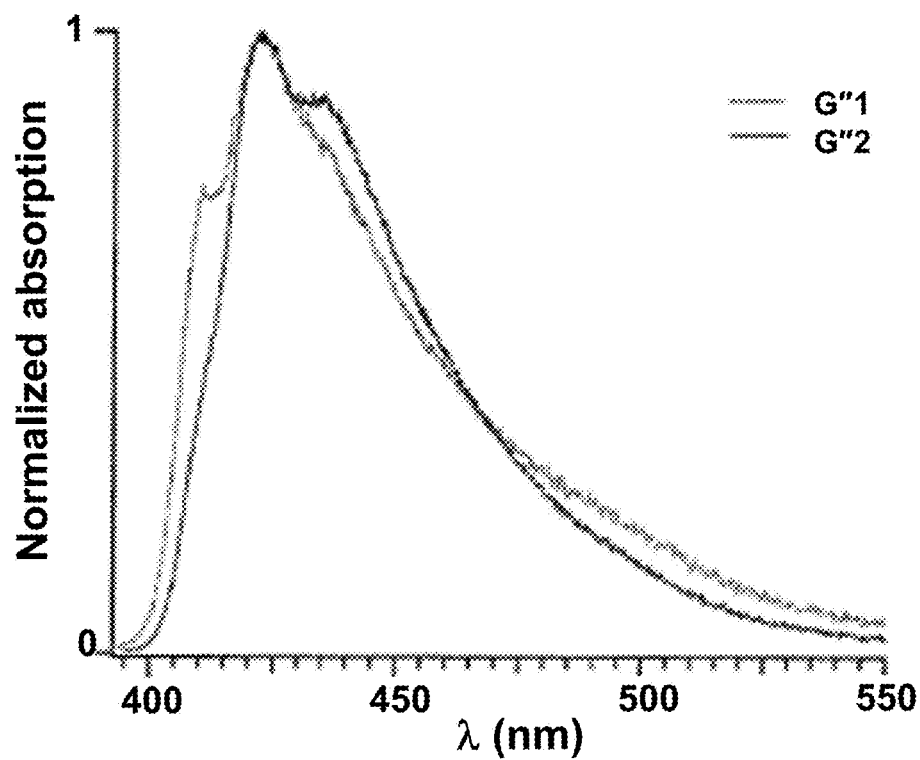
Figure 18:
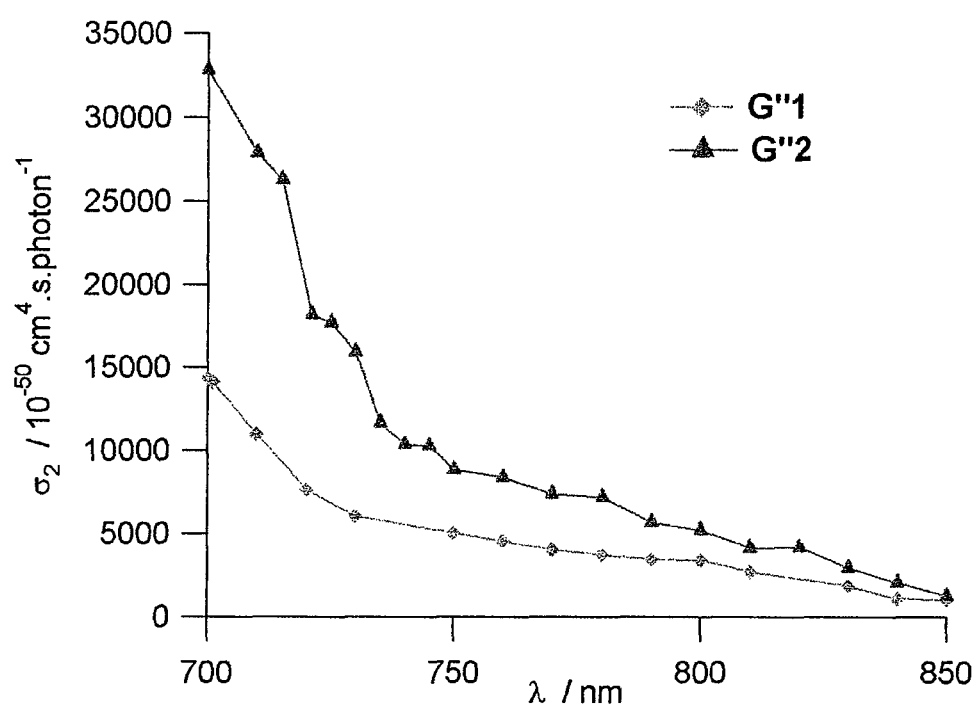
FIG. 18 shows the two-photon absorption spectra in toluene of these two compounds according to the invention, determined by TPEF measurements using a titanium-sapphire laser with femtosecond pulses.

The absorption and emission spectra in toluene for these two compounds are given in FIGS. 16 and 17, and their two-photon absorption spectra are given in FIG. 18.

The use of a core with 10 valences makes it possible to obtain, in fewer synthesis steps, dendrimers having a large number of fluorophores and very high effective two-photon absorption cross-sections. The dendrimer G"2 of generation 2 thus has effective TPA cross-sections $\sigma_2$ greater than dendrimer G3 of generation 3 of the series with a core with 6 valences. By contrast, it is noted that the nature and shape of the core with ten valences lead to lower fluorescence quantum efficiencies ($\Phi$) than those of the dendrimers having a core with 6 valences. However, it is noted that, advantageously, this quantum efficiency $\Phi$ increases with the generation of the dendrimer.

The embodiments of the invention described here are in no way limiting. In particular, it is possible to envisage the grafting, on the compounds, of other types of functional groupings making them water-soluble. These can in particular be pyridinium, carboxylate or sulfonate groups or polyethyleneglycol chains. It is also possible to graft other types of functional groups aside from those enabling water-solubility. These groups can be grafted on a generation other than the generation forming the outer layer of the compounds.

The compounds can include chromophoric or non-chromophoric groups of various types in the same compound.

The layer(s) of chromophoric patterns can be internal or external.

The compounds may or may not have one or more outer generations for protecting the chromophoric patterns.

The compounds according to the invention can have a plurality of cores each generating a tree structure of chromophoric and non-chromophoric patterns and bound to one another either directly or by means of chromophoric or non-chromophoric patterns.

The invention claimed is:

1. Fluorescent chemical compound formed by a dendrimer of n generation(s), in which n is a non-zero integer, having:
    at least one central core (N) of valence m chosen from the group consisting of:

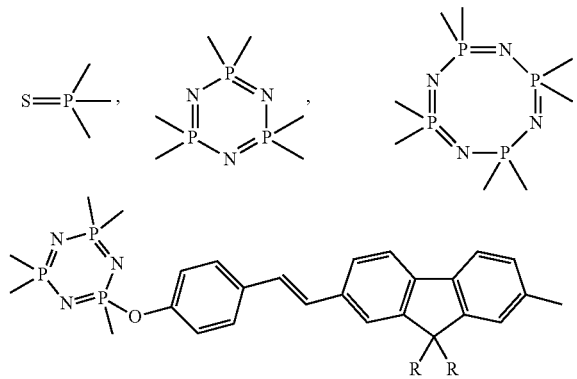

-continued

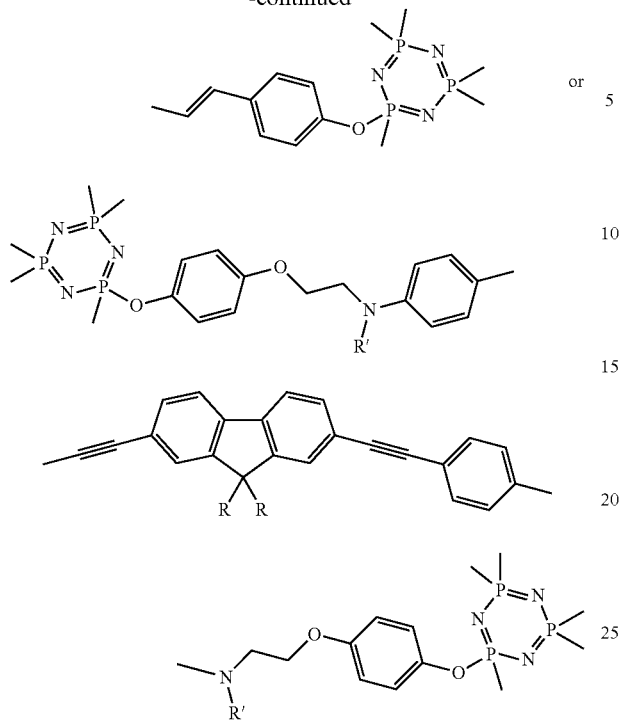

wherein R and R' are identical or different and designate a radical chosen from the group consisting of hydrogen, and $C_1$ to $C_{25}$ alkyl radicals;

at least one first non-chromophoric pattern (X) of valence m' chosen from the group consisting of:

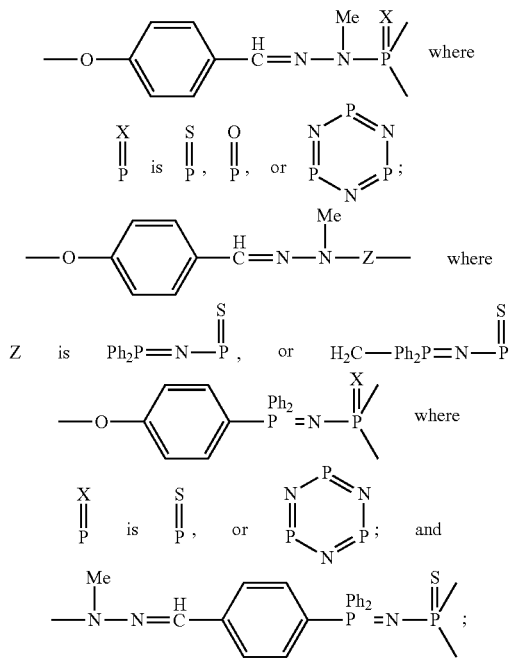

m patterns (X) being directly bound to said central core (N) and/or
x patterns forming at least one generation of said dendrimer; and at least one second pattern (Y) having two-photon absorption properties, of valence m", m chromophoric patterns (Y) being directly bound to said central core (N) and/or y patterns (Y') belonging to, or forming at least one generation of said dendrimer, in which said chromophoric pattern (Y) is formed by a multiphoton chromophoric radical (Y1) bound to at least one grafting appendage (Y2).

in which said chromophoric radical (Y1) has one of the following two structures:

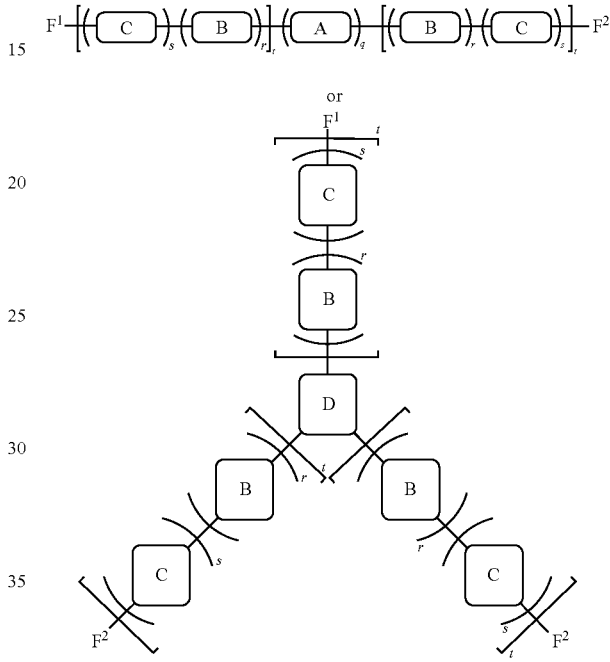

in which $F^1$ and $F^2$ are identical or different and designate an electroactive grouping (electron donor or acceptor), with $F^1$ being bound to a grafting appendage and $F^2$ being bound to 0, 1 or 2 grafting appendages, and wherein $F^1$ and $F^2$ are chosen from:

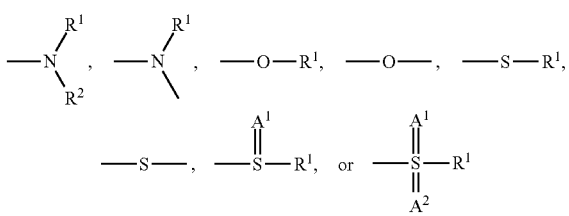

wherein $R^1$ and $R^2$ are identical or different and designate either a grafting appendage (Y2), or a radical chosen from the group consisting of hydrogen, $C_1$ to $C_{25}$ alkyl radicals, $(CH_2)_{ml}$—$SO_3M$, $(CH_2)_{ml}NAlk_3^+$, $(CH_2)_{ml}$—$(OCH_2$—$CH_2)_p$—OH, with M being an alkaline metal and ml being equal to 0 or being an integer between 1 and 12, and p being an integer between 1 and 25;

$A^1$ and $A^2$ are identical or different, representing O, NH, NAlk, $NCF_3$;

and in which,

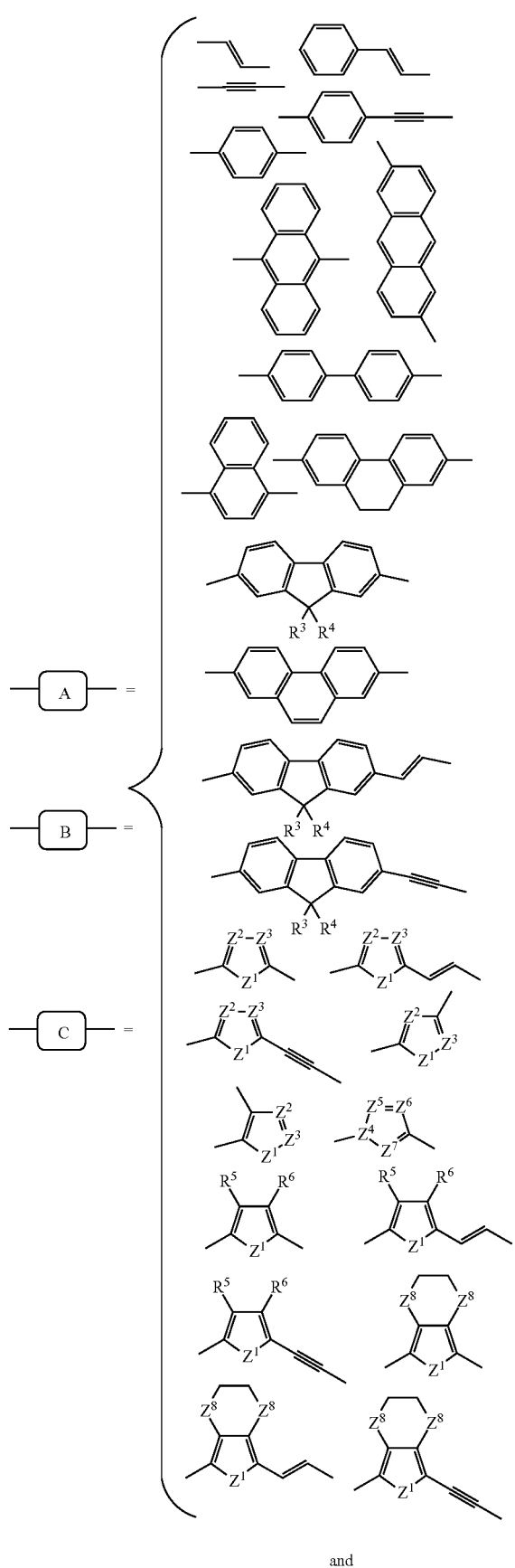

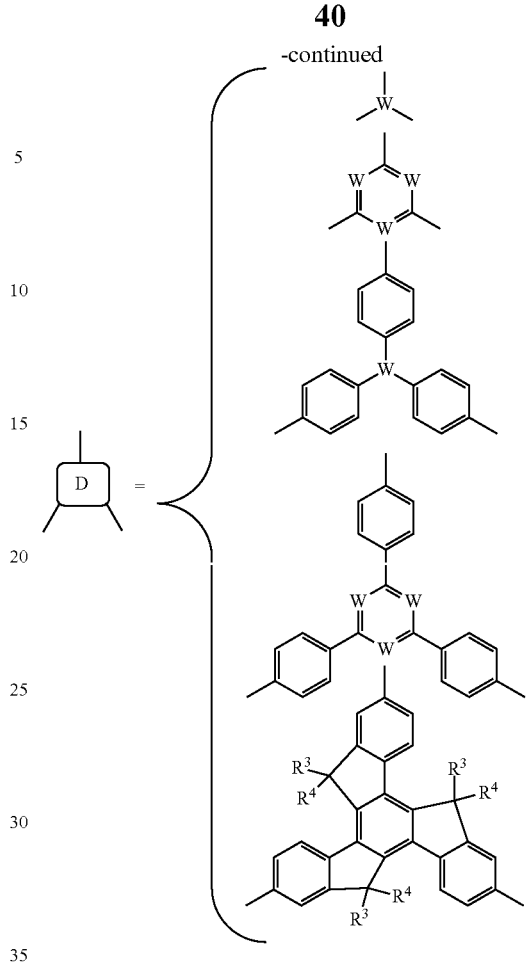

$R^3$ and $R^4$ are identical or different and designate a radical chosen from the group consisting of: hydrogen, $C_1$ to $C_{25}$ alkyl radicals, $(CH_2)_{ml}$—$SO_3M$, $(CH_2)_{ml}NAlk_3^+$, $(CH_2)_{ml}$—$(OCH_2$—$CH_2)_p$—OH, with M being an alkaline metal and ml being equal to 0 or being an integer between 1 and 12, and p being an integer between 1 and 25;

$R^5$ and $R^6$ are identical or different, each representing an OH, OAlk, OAr, SH, SAlk, or SAr radical;

$Z^1$, representing O, S, NH, NAlk, NAr, PH, PAlk or PAr;

$Z^2$, $Z^3$ each representing CH, CAlk or N;

$Z^4$ representing N or P;

$Z^5$, $Z^6$, $Z^7$ each representing CH, CAlk or N;

$Z^8$ representing O or S;

q being an integer between 1 and 7;
r being an integer between 1 and 7;
s being an integer between 0 and 7;
t being an integer between 1 and 7;
W being CH or B or N or P or PO,
and,
said grafting appendage (Y2) is chosen from:

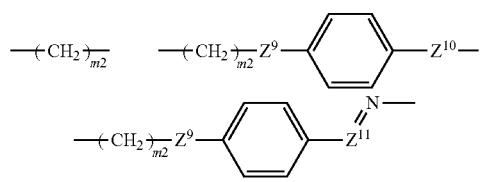

-continued

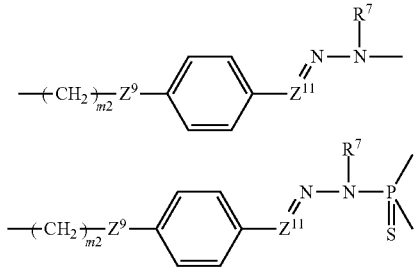

$R^7$ is a radical chosen from the group consisting of: hydrogen, $C_1$ to $C_{25}$ alkyl radicals, $(CH_2)_{m1}$—$SO_3M$, $(CH_2)_{m1}$ $NAlk_3^+$, $(CH_2)_{m1}$—$(OCH_2$—$CH_2)_p$OH, with M being an alkaline metal and m1 being equal to 0 or being an integer between 1 and 12, and p being an integer between 1 and 25, with m2 being an integer between 0 and 12;
$Z^9$ and $Z^{10}$, identical or different, representing O, S, NH, NAlk, and NAr; and
$Z^{11}$, representing CH, CAlk, CAr, $PAlk_2$, and $PAr_2$.

2. Compound according to claim 1, characterized in that n is greater than 3.

3. Compound according to claim 1, characterized in that said core (N) is

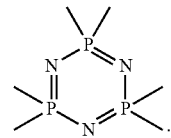

4. Compound according to claim 1, characterized in that said pattern (Y) is chosen from the group consisting of:

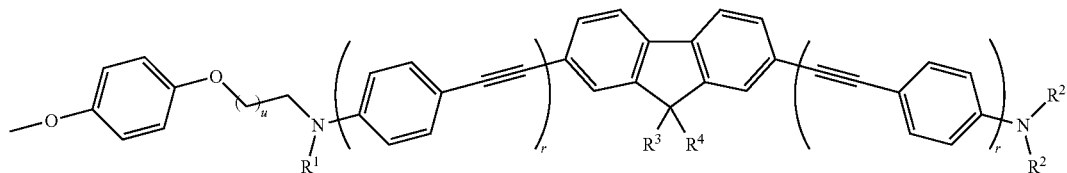

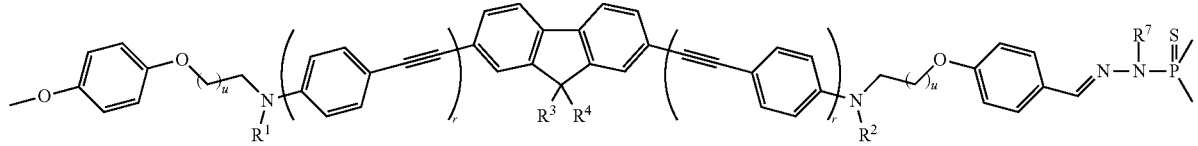

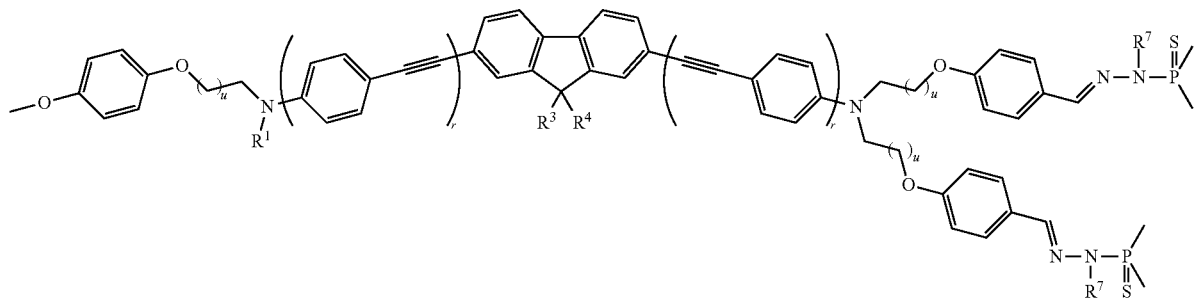

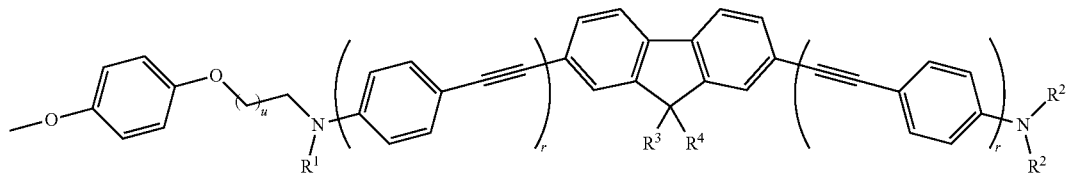

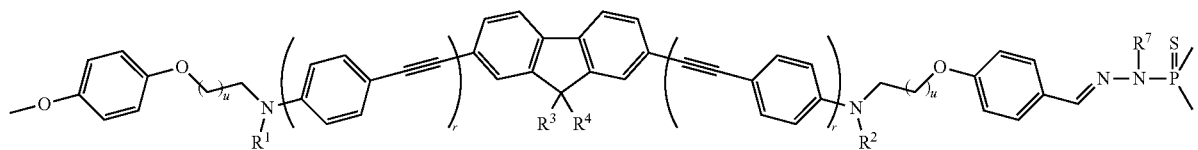

-continued

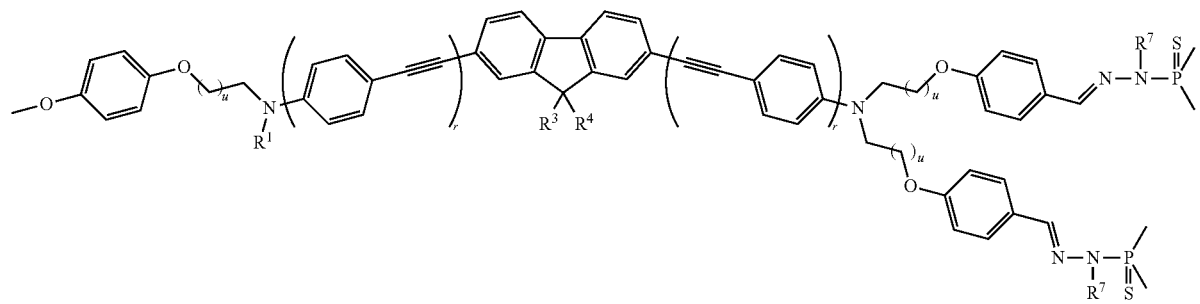

in which $R^1$, $R^2$, $R^3$, $R^4$, $R^7$ and r have the same meanings as in claim 1; and u is an integer between 1 and 11.

5. Compound according to claim 1, characterized in that said dendrimer has at least one third pattern (Z) forming the external layer of the generation Gn of said dendrimer and presenting solubilization properties of the dendrimer either in water or in organic solvents.

6. Compound according to claim 5, characterized in that said pattern (Z) is an ammonia or pyridinium or carboxylate or sulfonate pattern or a polyethyleneglycol chain.

7. Compound according to claim 5, characterized in that it satisfies any one of the following formulas:

G'2

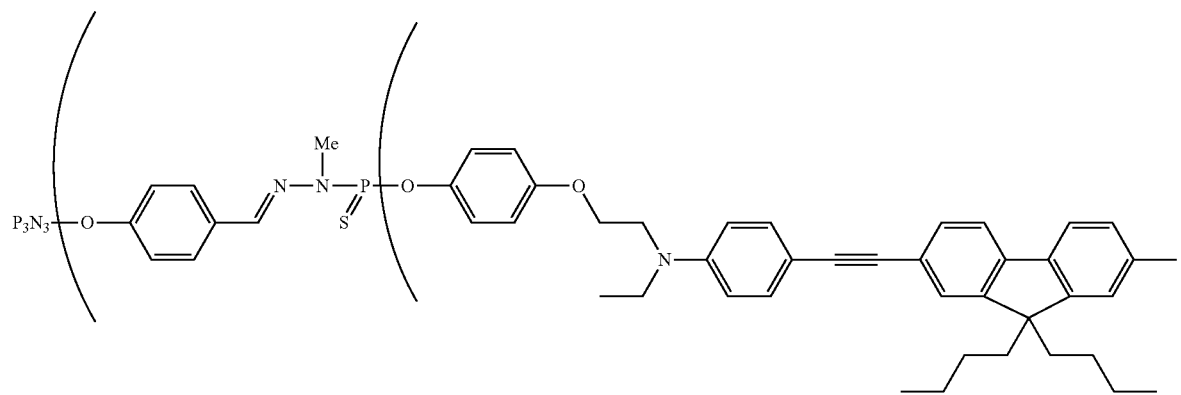

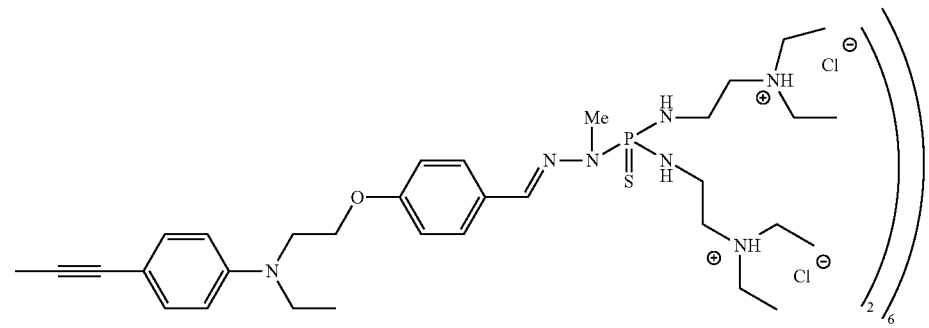

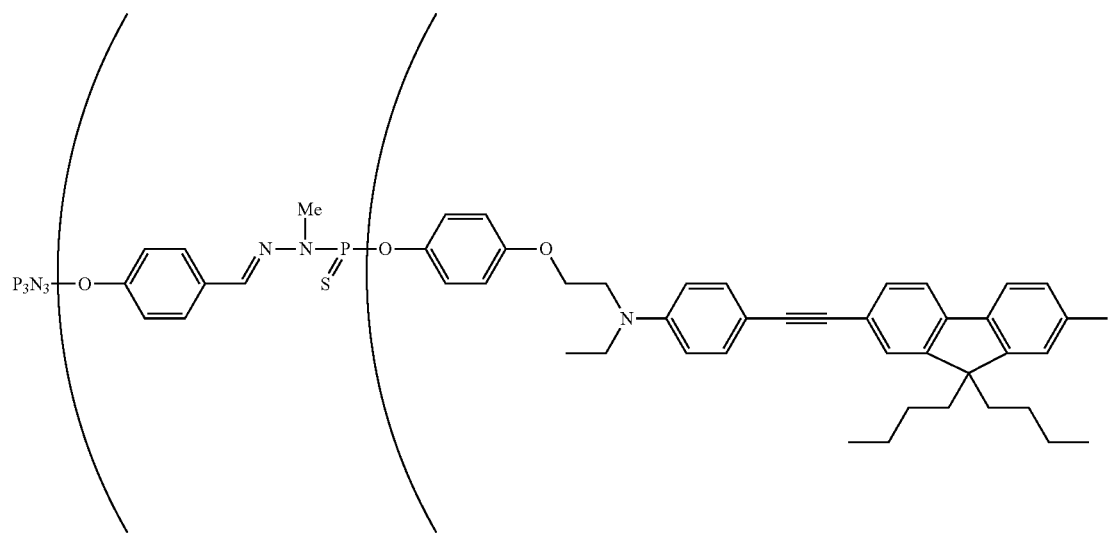
G'3
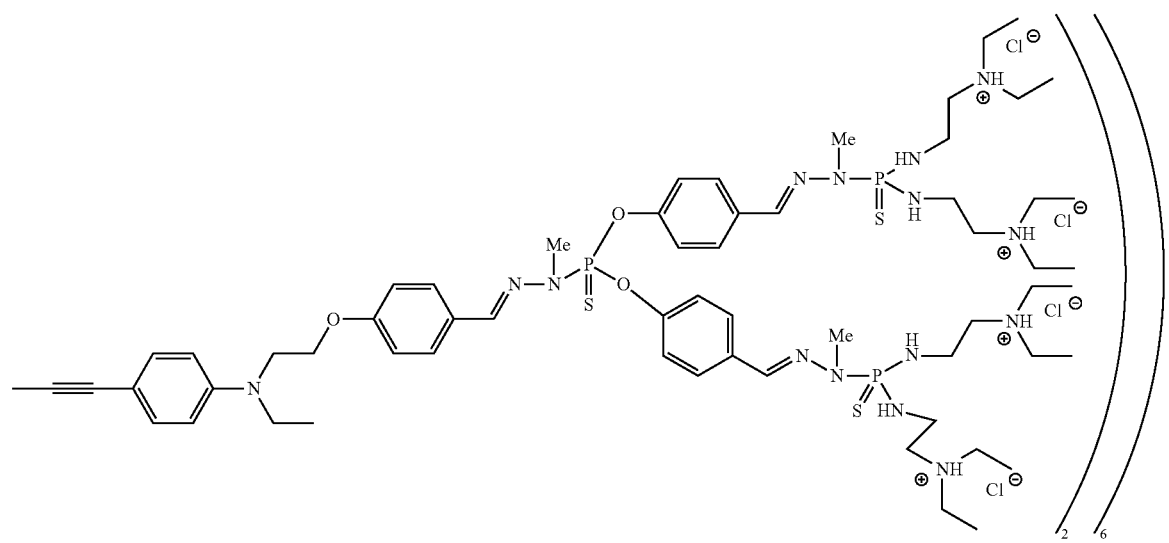
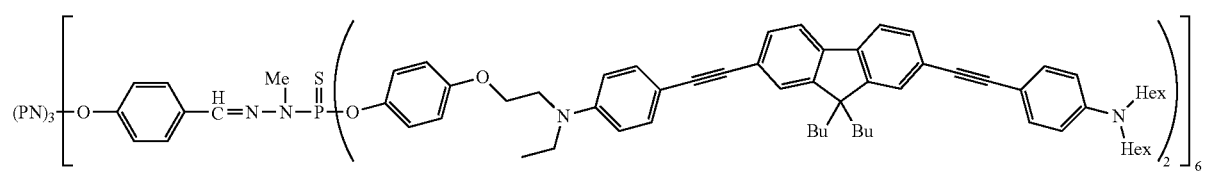
G1
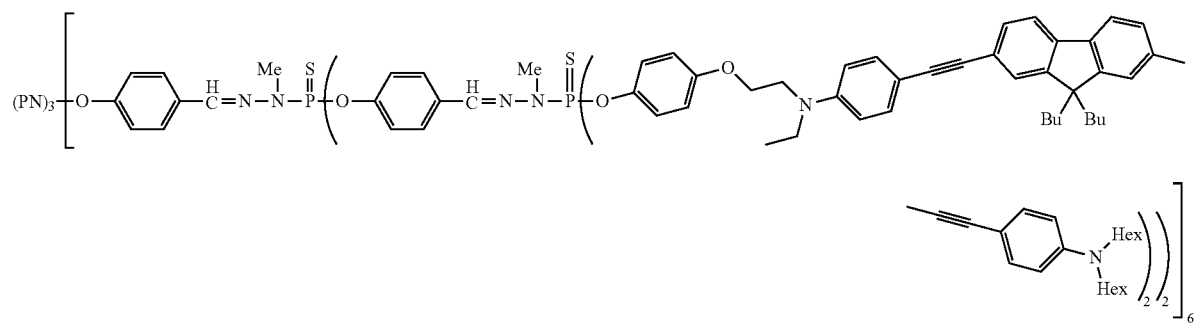
G2

-continued
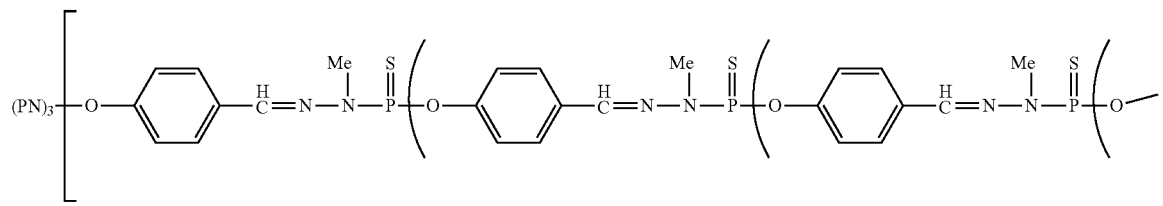
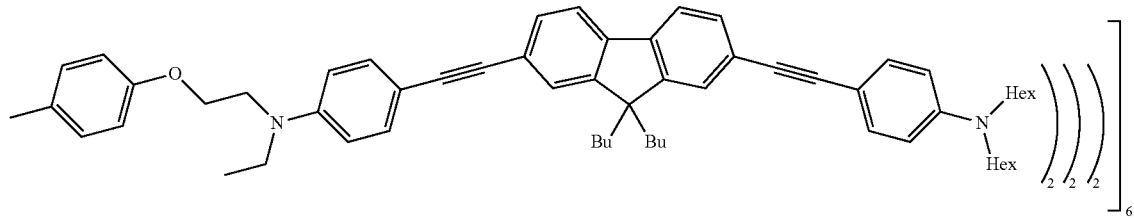
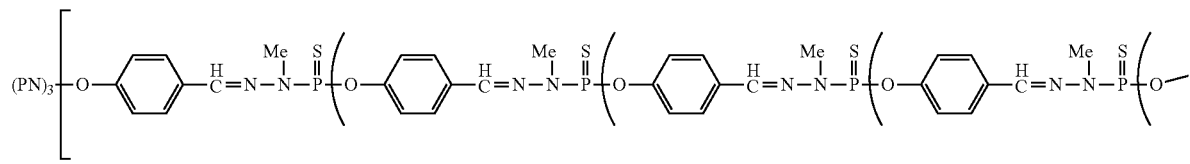
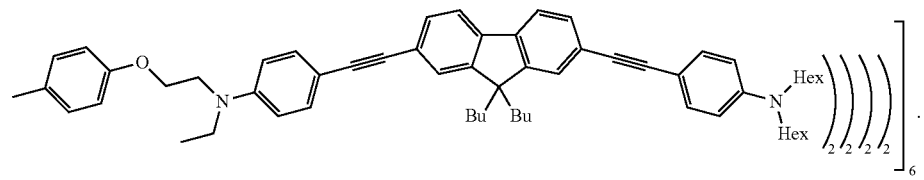
8. Compound according to claim 5, characterized in that it has either one of the following formulas:
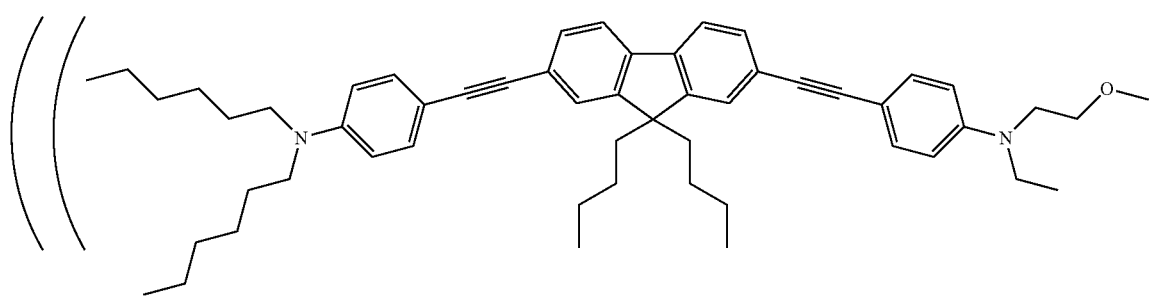
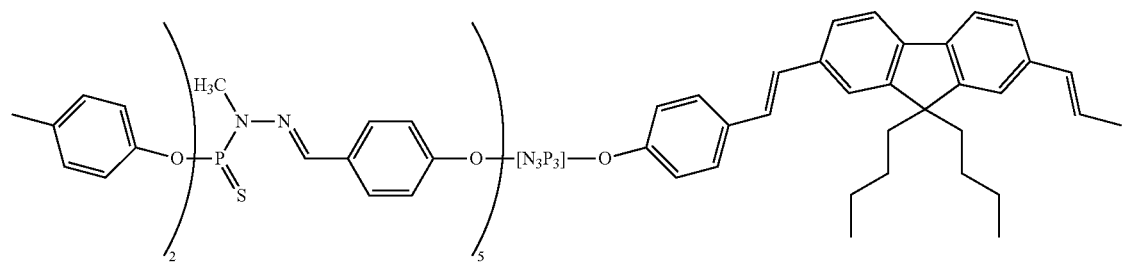

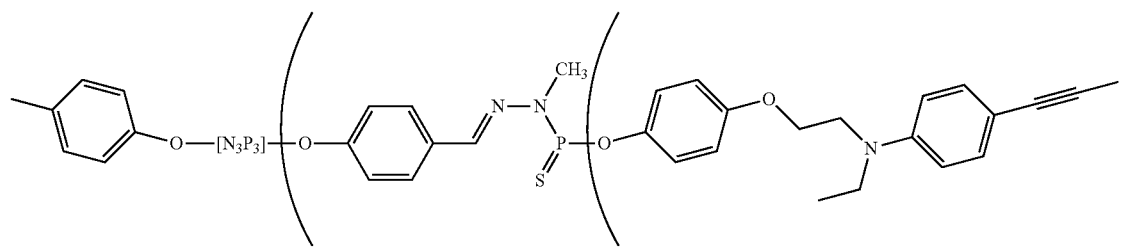
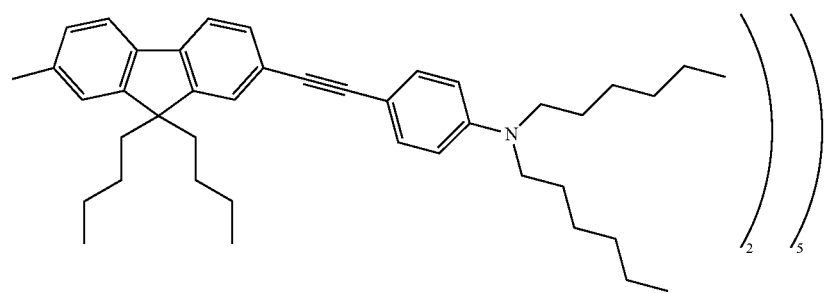
G″2
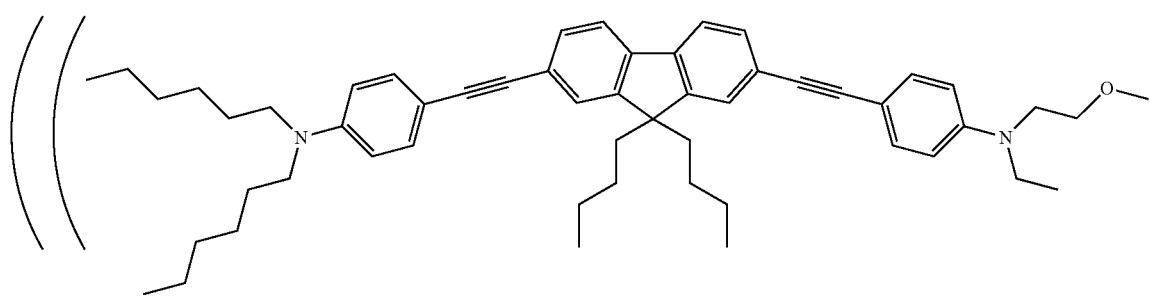
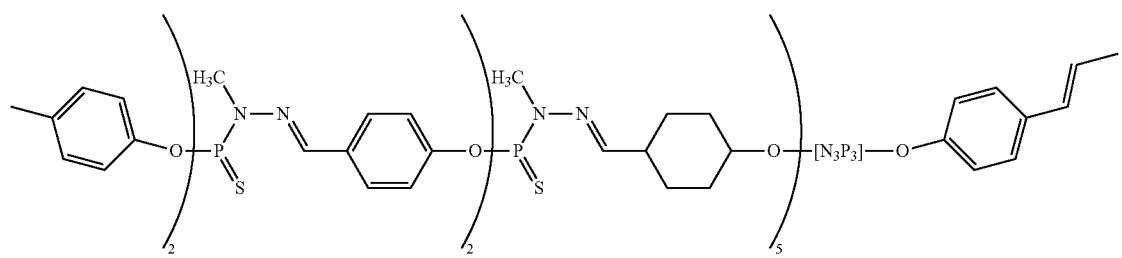
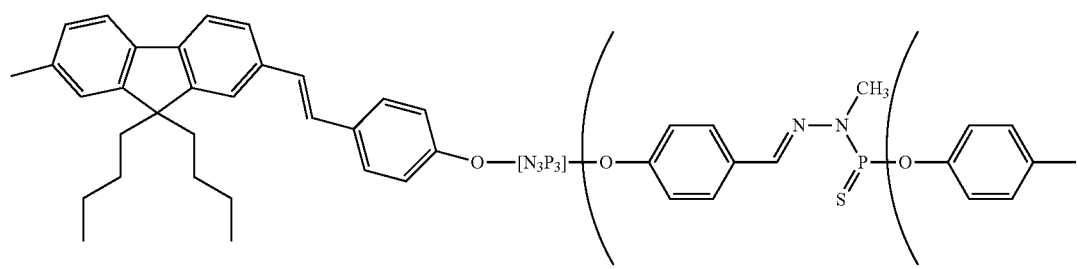

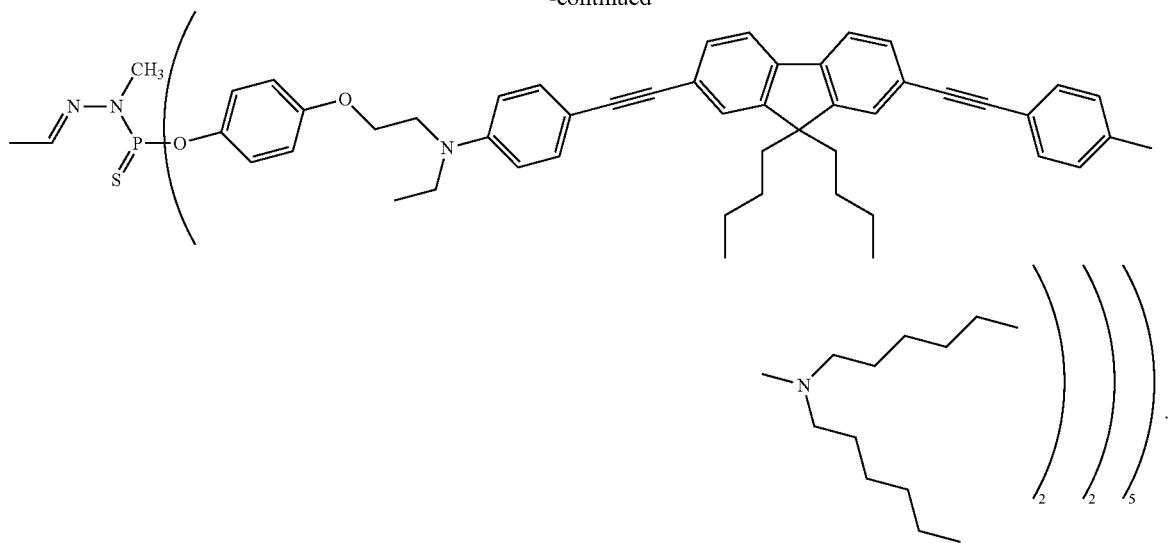

9. Compound according to claim 1, characterized in that it has two cores with identical or different valences, bound directly to one another or bound to one another by means of a pattern (Y) having two-photon absorption properties.

10. Compound according to claim 1, characterized in that it has at least two types of pattern (Y) having two-photon absorption properties.

11. Compound according to claim 10, characterized in that the various types of patterns with two-photon absorption properties have different wavelength emission properties.

12. Compound according to claim 11, characterized in that the various types of patterns have two-photon absorption properties with different wavelength emission properties of which the sum leads to the emission of a white light.

* * * * *

UNITED STATES PATENT AND TRADEMARK OFFICE
CERTIFICATE OF CORRECTION

PATENT NO. : 8,535,643 B2  
APPLICATION NO. : 12/160612  
DATED : September 17, 2013  
INVENTOR(S) : Blanchard-Desce et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1347 days.

Signed and Sealed this

Fifteenth Day of September, 2015

Michelle K. Lee
*Director of the United States Patent and Trademark Office*